United States Patent [19]
Lyssikatos

[11] Patent Number: 6,071,935
[45] Date of Patent: Jun. 6, 2000

[54] DERIVATIVES OF 2-(2-OXO-ETHYLIDENE)-IMIDAZOLIDIN-4-ONE AND THEIR USE AS FARNESYL PROTEIN TRANSFERASE INHIBITORS

[75] Inventor: Joseph P. Lyssikatos, Gales Ferry, Conn.

[73] Assignee: Pfizer Inc., New York, N.Y.

[21] Appl. No.: 09/202,796

[22] PCT Filed: May 22, 1997

[86] PCT No.: PCT/IB97/00584

§ 371 Date: Oct. 7, 1999

§ 102(e) Date: Oct. 7, 1999

[87] PCT Pub. No.: WO97/49700

PCT Pub. Date: Dec. 31, 1997

Related U.S. Application Data

[60] Provisional application No. 60/020,696, Jun. 27, 1996.

[51] Int. Cl.[7] .................. C07D 401/14; A61K 31/44; A61K 31/415
[52] U.S. Cl. .................. 514/333; 514/398; 546/256; 548/324.1
[58] Field of Search .................. 546/256; 548/324.1; 514/333, 398

[56] References Cited

FOREIGN PATENT DOCUMENTS

95/29909 11/1995 WIPO .................. 514/398

OTHER PUBLICATIONS

Graham et al, Journal of Medicinal Chemistry, vol. 37, No. 6, p. 725–732, Mar. 1994.

*Primary Examiner*—Zinna Northington Davis
*Attorney, Agent, or Firm*—Peter C. Richardson; Paul H. Ginsburg; Seth Jacobs

[57] ABSTRACT

The present invention relates to compounds of the formula

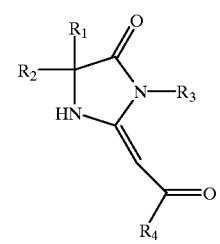

I wherein $R_1$, $R_2$, $R_3$ and $R_4$ are as defined herein. The invention also relates to pharmaceutical compositions containing the compounds of formula I and to methods of inhibiting abnormal cell growth, including cancer, in a mammal by administering the compounds of formula I to said mammal.

26 Claims, No Drawings

DERIVATIVES OF 2-(2-OXO-ETHYLIDENE)-IMIDAZOLIDIN-4-ONE AND THEIR USE AS FARNESYL PROTEIN TRANSFERASE INHIBITORS

This application is a 371 of PCT/IB97/0584 filed May 22, 1997 which claims the benefit of priority to Provisional Application Ser. No. 60/020,696 filed Jun. 27, 1996.

BACKGROUND OF THE INVENTION

This invention relates to a series of novel derivatives of 2-(2-oxo-ethylidene)-imidazolidin-4-one that exhibit activity as inhibitors of the enzyme farnesyl protein transferase and are believed to be useful as anti-cancer and anti-tumor agents. This invention also relates to methods of using such compounds in the treatment or prevention of cancer in a mammal, in particular a human, and to pharmaceutical compositions containing such compounds.

Other compounds that inhibit farnesyl protein transferase and are believed to be useful as anti-cancer and anti-tumor agents are referred to in International Patent Application PCT/US92/11292, which designates the United States and was published on Jul. 22, 1993 as WO 93/14085, U.S. Pat. No. 4,876,259, which issued on Oct. 24, 1989, International Patent Application PCT/IB95/00189, which designates the United States and was filed on Mar. 20, 1995, U.S. patent application Ser. No. 08/236,743, which was filed on Apr. 29, 1994, and U.S. Provisional Application entitled "Adamantyl Substituted Oxindoles As Pharmaceutical Agents," which was filed on May 28, 1996, in the name of R. A. Volkmann and J. P. Lyssikatos. The foregoing patent and patent applications are incorporated herein by reference in their entireties.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anti-cancer agents for tumors in which Ras contributes to transformation. Mutated, oncogenic forms of Ras are frequently found in many human cancers, most notably in more than 50% of colon and pancreatic carcinomas (Kohl et al., Science, Vol. 260, 1834 to 1837, 1993).

SUMMARY OF THE INVENTION

The present invention relates to compounds of the formula I

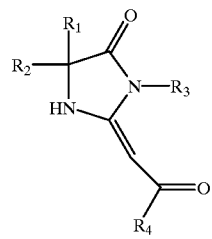

and to pharmaceutically acceptable salts thereof, wherein:

$R_1$ and $R_2$ are independently selected from the group consisting of $-(CH_2)_p$(5–10 membered heterocyclyl), $-(CH_2)_p(C_6-C_{10}$ aryl), allyl, propargyl and $C_1-C_6$ alkyl wherein p is 0 to 3, said alkyl and the alkyl moieties of said $R_1$ and $R_2$ groups are optionally substituted by 1 to 3 $R_9$ substituents, and the aryl and heterocyclyl moieties of said $R_1$ and $R_2$ groups are optionally substituted by 1 to 3 substituents independently selected from halo and $R_9$;

$R_3$ is $-(CH_2)_m$(1- or 2-adamantyl), $-(CH_2)_m(C_3-C_{10}$ cycloalkyl), $-(CH_2)_m(C_6-C_{10}$ aryl), $C_1-C_{10}$ alkyl,

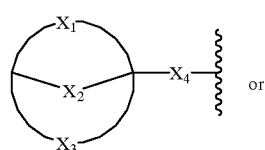

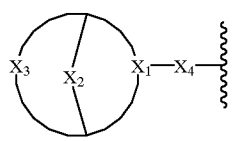

wherein m is 0 to 6, and said cycloalkyl and alkyl optionally contain 1 or 2 double or triple bonds;

$X_1$, $X_2$, and $X_3$ are each independently $C_1-C_7$ alkylene optionally containing 1 or 2 double or triple bonds, $X_4$ is a bond or $C_1-C_7$ alkylene optionally containing 1 or 2 double or triple bonds, and, in formula (Ib), the $X_4$ moiety is attached to the $X_1$ moiety at any available carbon in the $X_1$ moiety;

$R_4$ is $C_6-C_{10}$ aryl, 5–10 membered heterocyclyl or $C_1-C_6$ alkyl wherein each of said $R_4$ groups is optionally substituted by 1 to 3 $R_5$ substituents;

each $R_5$ is independently selected from the group consisting of halo, nitro, cyano, phenyl, $-C(O)OR_6$, $-SO_2NR_6R_7$, $-NR_6R_8$, $-C(O)R_6$, $-OR_6$, $-C(O)NR_6R_8$, $-OC(O)NR_6R_8$, $-NR_8C(O)NR_8R_6$, $-NR_8C(O)R_6$, $-NR_8C(O)O(C_1-C_4$ alkyl), $-C(NR_8)NR_8R_6$, $-C(NCN)NR_8R_6$, $-C(NCN)S(C_1-C_4$ alkyl), $-NR_8C(NCN)S(C_1-C_4$ alkyl), $-NR_8C(NCN)NR_8R_6$, $-NR_8SO_2(C_1-C_4$ alkyl), $-S(O)_n(C_1-C_4$ alkyl) wherein n is 0 to 2, $-NR_8C(O)C(O)NR_8R_6$, $-NR_8C(O)C(O)R_8$, thiazolyl, imidazolyl, oxazolyl, pyrazolyl, triazolyl, tetrazolyl, and $C_1-C_4$ alkyl optionally substituted by 1 to 3 fluoro substituents;

each $R_6$ and $R_7$ is independently hydrogen or $C_1-C_4$ alkyl;

each $R_8$ is independently $R_6$ or $-OR_6$; and, each $R_9$ is independently selected from cyano, $R_6$, —$OR_6$, —$OC(O)R_6$, —$C(O)OR_6$, —$C(O)NR_6R_7$, —$NR_6R_7$, —$NR_6R_8$, —$SO_2NR_6R_7$, and $C_1$–$C_4$ alkyl substituted by hydroxy.

Preferred compounds of formula I include those wherein $R_1$ and $R_2$ are both —$(CH_2)_p$(5–10 membered heterocyclyl) wherein p is 1 or 2. More preferably, $R_1$ and $R_2$ are 2-, 3- or 4-pyridinylmethyl. Most preferred are those compounds of formula I wherein $R_1$ and $R_2$ are both 4-pyridinylmethyl.

Other preferred compounds of formula I include those wherein $R_3$ is —$(CH_2)_m$(pinane) wherein m is 0, 1 or 2, and, more preferably, those wherein $R_3$ is pinanemethyl.

Other preferred compounds of formula I include those wherein $R_3$ is (Ia)

(Ib)

wherein $X_1$, $X_2$, $X_3$ and $X_4$ are as defined above.

Other preferred compounds of formula I include those wherein $R_4$ is phenyl optionally substituted by 1 to 3 $R_5$ substituents.

Specific preferred compounds of formula I wherein $R_1$ and $R_2$ are both 4-pyridinylmethyl and $R_3$ is —$(CH_2)_m$ (pinane), wherein m is 0 to 2, include the following:

2-[2-(4-Bromo-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one;

4-{[5-Oxo-4,4-bis-pyridin-4-ylmethyl-1-(2,6,6-trimethyl-bicyclo[3.1.1]hept-3-ylmethyl)-imidazolidin-2-ylidene]-acetyl}-benzonitrile;

2-[2-(4-Chloro-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one;

2-[2-(3,4-Dichloro-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one;

2-[2-(3-Nitro-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one;

2-[2-(4-Methoxy-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one;

2-[2-(3-Methoxy-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one;

2-[2-(2-Methoxy-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one;

2-(2-Biphenyl-4-yl-2-oxo-ethylidene)-5,5-bis-pyridin-4-ylmethyl-3-(2,6,6-trimethyl-bicyclo[3.1.1]hept-3-ylmethyl)-imidazolidin-4-one;

2-(2-Naphthalen-2-yl-2-oxo-ethylidene)-5,5-bis-pyridin-4-ylmethyl-3-(2,6,6-trimethyl-bicyclo[3.1.1]hept-3-ylmethyl)-imidazolidin-4-one;

2-[2-(4-Fluoro-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one;

2-[2-(2,4-Difluoro-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one;

4-{[5-Oxo-4,4-bis-pyridin-4-ylmethyl-1-(2,6,6-trimethyl-bicyclo[3.1.1]hept-3-yl)-imidazolidin-2-ylidene]-acetyl}-benzonitrile;

2-[2-(4-Nitro-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one;

2-[2-Oxo-2-phenyl-ethylidene]-5,5-bis-pyridin-4-ylmethyl-3-(2,6,6-trimethyl-bicyclo[3.1.1]hept-3-ylmethyl)-imidazolidin-4-one;

2-{2-Oxo-2-[4-(2H-tetrazol-5-yl)-phenyl]-ethylidene}-5,5-bis-pyridin-4-ylmethyl-3-(2,6,6-trimethyl-bicyclo[3.1.1]hept-3-ylmethyl)-imidazolidin-4-one;

3-{[5-Oxo-4,4-bis-pyridin-4-ylmethyl-1-(2,6,6-trimethyl-bicyclo[3.1.1]hept-3-ylmethyl)-imidazolidin-2-ylidene]-acetyl}-benzonitrile;

4-{[5-Oxo-4,4-bis-pyridin-4-ylmethyl-1-(2,6,6-trimethyl-bicyclo[3.1.1]hept-3-ylmethyl)-imidazolidin-2-ylidene]-acetyl}-benzoic acid ethyl ester;

2-[2-Oxo-2-(4-trifluoromethyl-phenyl)-ethylidene]-5,5-bis-pyridin-4-ylmethyl-3-(2,6,6-trimethyl-bicyclo[3.1.1]hept-3-ylmethyl)-imidazolidin-4-one; and, 2-[2-(4-Methanesulphonyl-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one.

Other specific preferred compounds of formula I wherein $R_1$ and $R_2$ are both 4-pyridinylmethyl and $R_3$ is an aliphatic bicyclo moiety (other than pinane) of the formula (Ia) or (Ib), wherein (Ia) and (Ib) are as defined above, include the following:

4-{[1-(6,6-Dimethyl-bicyclo[3.1.1]hept-2-ylmethyl)-5-oxo-4,4-bis-pyridin-4-ylmethyl-imidazolidin-2-ylidene]-acetyl}-benzonitrile;

4-[(1-Bicyclo[2.2.2]oct-1-ylmethyl-5-oxo-4,4-bis-pyridin-4-ylmethyl-imidazolidin-2-ylidene)-acetyl]-benzonitrile;

4-{[1-(2-Ethyl-6,6-dimethyl-bicyclo[3.1.1]hept-3-ylmethyl)-5-oxo-4,4-bis-pyridin-4-ylmethyl-imidazolidin-2-ylidene]-acetyl}-benzonitrile;

4-{[1-(2-Benzyl-6,6-dimethyl-bicyclo[3.1.1]hept-3-ylmethyl)-5-oxo-4,4-bis-pyridin-4-ylmethyl-imidazolidin-2-ylidene]-acetyl}-benzonitrile;

4-{[1-(2-isopropenyl-6,6-dimethyl-bicyclo[3.1.1]hept-3-ylmethyl)-5-oxo-4,4-bis-pyridin-4-ylmethyl-imidazolidin-2-ylidene]-acetyl}-benzonitrile;

4-{[1-(2-isopropyl-6,6-dimethyl-bicyclo[3.1.1]hept-3-ylmethyl)-5-oxo-4,4-bis-pyridin-4-ylmethyl-imidazolidin-2-ylidene]-acetyl}-benzonitrile;

4-({1-[2-(1-Methoxyimino-ethyl)-6,6-dimethyl-bicyclo[3.1.1]hept-3-ylmethyl]-5-oxo-4,4-bis-pyridin-4-ylmethyl-imidazolidin-2-ylidene}-acetyl)-benzonitrile;

4-{[1-(6,6-Dimethyl-2-methylene-bicyclo[3.1.1]hept-3-ylmethyl)-5-oxo-4,4-bis-pyridin-4-ylmethyl-imidazolidin-2-ylidene]-acetyl}-benzonitrile;

4-{[1-(2-Hydroxy-2-hydroxymethyl-6,6-d imethyl-bicyclo[3.1.1]hept-3-ylmethyl)-5-oxo-4,4-bis-pyridin-4-ylmethyl-imidazolidin-2-ylidene]-acetyl}-benzonitrile; and, 4-{[1-(6,6-Dimethyl-2-oxo-bicyclo[3.1.1]hept-3-ylmethyl)-5-oxo-4,4-bis-pyridin-4-ylmethyl-imidazolidin-2-ylidene]-acetyl}-benzonitrile.

Other specific preferred compounds of formula I include the following:

3-tert-Butyl-2-(2-oxo-2-phenyl-ethylidene)-5,5-bis-pyridin-4-ylmethyl-imidazolidin-4-one;

4-{[1-(2,2-Dimethyl-propyl)-5-oxo-4,4-bis-pyridin-4-ylmethyl-imidazolidin-2-ylidene]-acetyl}-benzonitrile;

4-{[1-(2-Adamantan-1-yl-ethyl)-5-oxo-4,4-bis-pyridin-4-ylmethyl-imidazolidin-2-ylidene]-acetyl}-benzonitrile;

3-Cyclohexyl-2-(2-oxo-2-phenyl-ethylidene)-5,5-bis-pyridin-4-ylmethyl-imidazolidin-4-one;

4-[(1-Adamant-1-ylmethyl-5-oxo-4,4-bis-pyridin-4-ylmethyl-imidazolidin-2-ylidene)-acetyl]-benzonitrile;

4-[(1-Cyclohexylmethyl-5-oxo-4,4-bis-pyridin-4-ylmethyl-imidazolidin-2-ylidene)-acetyl]-benzonitrile;

3-Hexyl-2-(2-oxo-2-phenyl-ethylidene)-5,5-bis-pyridin-4-ylmethyl-imidazolidin-4-one;

3-Napthalen-1-yl-2-(2-oxo-2-phenyl-ethylidene)-5,5-bis-pyridin-4-ylmethyl-imidazolidin-4-one;

3-Adamantan-1-yl-2-(2-oxo-2-phenyl-ethylidene)-5,5-bis-pyridin-4-ylmethyl-imidazolidin-4-one;

3-Adamantan-1-yl-2-[2-(4-nitro-phenyl)-2-oxo-ethylidene-5,5-bis-pyridin-4-ylmethyl-imidazolidin-4-one;

4-[(1-Benzyl-5-oxo-4,4-bis-pyridin-4-ylmethyl-imidazolidin-2-ylidene)-acetyl]-benzonitrile;

4-[(1-Ally-5-oxo-4,4-bis-pyridin-4-ylmethyl-imidazolidin-2-ylidene)-acetyl]-benzonitrile;

4-[(1-Methyl-5-oxo-4,4-bis-pyridin-4-ylmethyl-imidazolidin-2-ylidene)-acetyl]-benzonitrile;

4-{[1-(2,2-Diethoxy-ethyl)-5-oxo-4,4-bis-pyridin-4-ylmethyl-imidazolidin-2-ylidene]-acetyl}-benzonitrile;

4-[(1-Adamantan-2-ylmethyl-5-oxo-4,4-bis-pyridin-4-ylmethyl-imidazolidin-2-ylidene)-acetyl]-benzonitrile;

4-[(1-Adamantan-2-yl-5-oxo-4,4-bis-pyridin-4-ylmethyl-imidazolidin-2-ylidene)-acetyl]-benzonitrile;

4-[(5-Oxo-1-phenyl-4,4-bis-pyridin-4-ylmethyl-imidazolidin-2-ylidene)-acetyl]-benzonitrile; and, 4-{[4-tert-Butyl-phenyl-5-oxo-4,4-bis-pyridin-4-ylmethyl-imidazolidin-2-ylidene)-acetyl]-benzonitrile.

This invention also relates to a method of inhibiting the abnormal growth of cells in a mammal, including a human, comprising administering to said mammal an amount of a compound of the formula 1, as defined above, or a pharmaceutically acceptable salt thereof, that is effective in inhibiting farnesyl protein transferase.

This invention also relates to a method of inhibiting the abnormal growth of cells in a mammal, including a human, comprising administering to said mammal an amount of a compound of the formula I, as defined above, or a pharmaceutically acceptable salt thereof, that is effective in inhibiting abnormal cell growth.

This invention also relates to a pharmaceutical composition for inhibiting the abnormal growth of cells in a mammal, including a human, comprising an amount of a compound of the formula I, as defined above, or a pharmaceutically acceptable salt thereof, that is effective in inhibiting farnesyl protein transferase, and a pharmaceutically acceptable carrier.

This invention also relates to a pharmaceutical composition for inhibiting the abnormal growth of cells in a mammal, including a human, comprising an amount of a compound of the formula I, as defined above, or a pharmaceutically acceptable salt thereof, that is effective in inhibiting abnormal cell growth, and a pharmaceutically acceptable carrier.

"Abnormal cell growth", as used herein, refers to cell growth that is independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

Examples of such benign proliferative diseases are psoriasis, benign prostatic hypertrophy and restinosis.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties.

The term "alkoxy", as used herein, unless otherwise indicated, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl.

The term "pinane", as used herein, unless otherwise indicated, includes 2,6,6,-trimethyl-bicyclo[3.1.1.]hept-3-yl.

The term "heterocyclyl", as used herein, unless otherwise indicated, includes aromatic and non-aromatic heterocyclic groups containing one or more heteroatoms each selected from O, S and N. Such heterocyclic groups include benzo-fused ring systems and ring systems substituted with an oxo moiety. An example of a 5 membered heterocyclic group is thiazolyl, and an example of a 10 membered heterocyclic group is quinolinyl. Examples of non-aromatic heterocyclic groups are pyrrolidinyl, piperidino, morpholino, thiomorpholino and piperazinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. Heterocyclic groups having a fused benzene ring include benzimidazolyl.

The term "pharmaceutically acceptable salt(s)", as used herein, unless otherwise indicated, includes salts of acidic or basic groups that may be present in the compounds of formula I. For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. The preparation of such salts is described below.

Certain compounds of formula I may have asymmetric centers and therefore exist in different enantiomeric forms. All optical isomers and stereoisomers of the compounds of formula I, and mixtures thereof, are considered to be within the scope of the invention. With respect to the compounds of formula I, the invention includes the use of a racemate, one or more enantiomeric forms, one or more diastereomeric forms, or mixtures thereof. The compounds of formula I may also exist as tautomers. This invention relates to the use of all such tautomers and mixtures thereof.

Patients that can be treated with compounds of the formula I, as defined above, or pharmaceutically acceptable salts thereof, according to the methods of this invention include, for example, patients that have been diagnosed as having lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

Patients that can be treated with compounds of the formula I according to the methods of this invention also include patients suffering from abnormal cell growth, as defined above.

DETAILED DESCRIPTION OF THE INVENTION

The compounds of formula I are prepared as described below. In the reaction Scheme and discussion that follow, $R_1$, $R_2$, $R_3$, and $R_4$ are as defined above. The symbol "Me" in the following Scheme represents a methyl group.

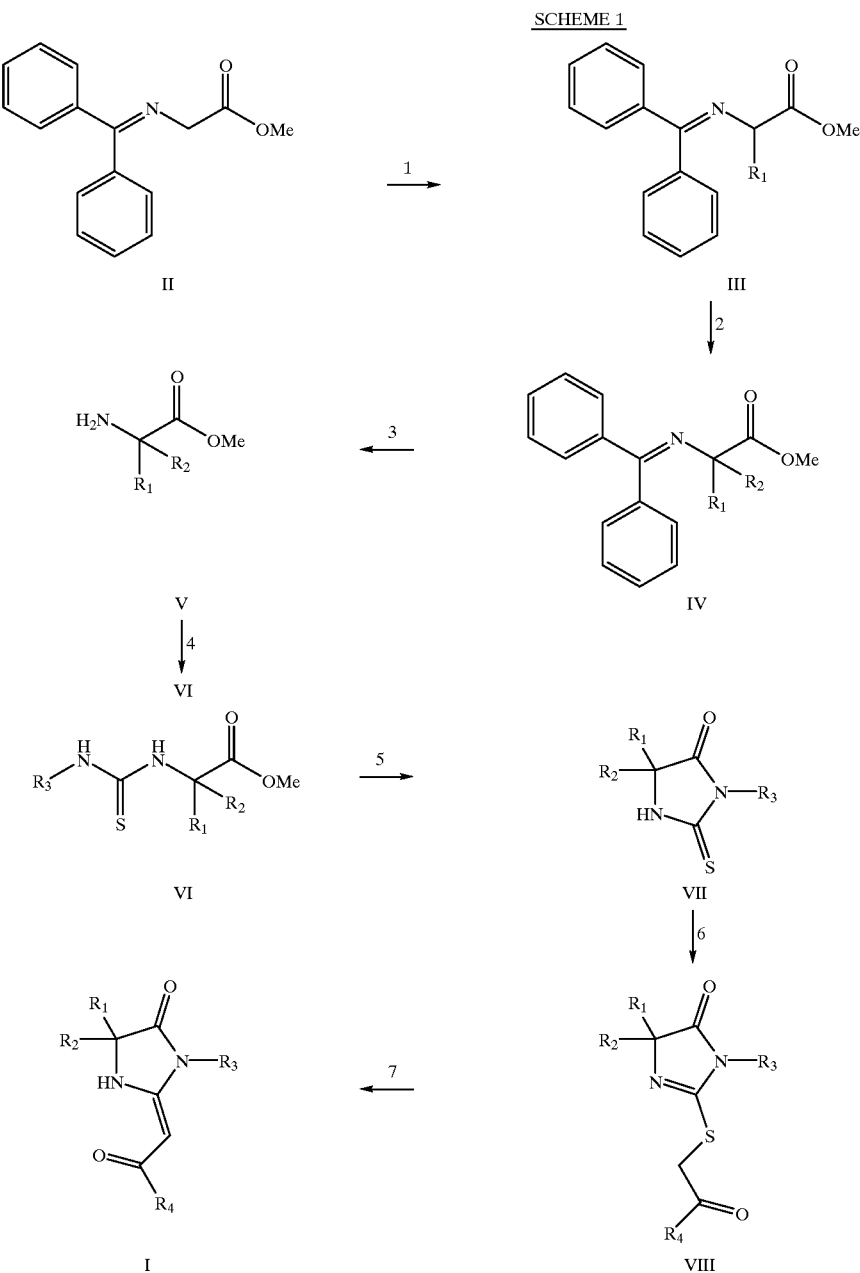

Scheme 1 illustrates the synthesis of the compounds of formula I. In step 1, the ester of formula II is reacted with potassium bis(trimethylsilyl)amide in tetrahydrofuran (THF) at a temperature of about −70° C. After stirring for about 30 minutes, a compound of the formula $R_1$—X, wherein $R_1$ is as defined above and X is an appropriate leaving group, such as chloride or bromide, is added to the reaction mixture, which is then allowed to warm to ambient temperature (20–25° C.). This results in the compound of formula III, which can be isolated or reacted in situ to form the compound of formula IV. In step 2, the $R_2$ substituent, wherein $R_2$ is as defined above, is added to the compound of formula III to provide the compound of formula IV according to the procedure of step 1, except that $R_2$—X is substituted for $R_1$—X.

In step 3, the intermediate of formula V is formed by reacting the compound of formula IV with an acid, preferably a mineral acid such as hydrochloric, nitric or sulfuric acid, in an organic co-solvent such as ethyl ether, THF or acetonitrile, preferably THF, at a temperature ranging from about −5° C. to 35° C., preferably from about 0° C. to ambient temperature.

Steps 4 and 5 may be done as a single step or as separate steps. In general, the imidazolidine intermediate of formula VII is formed by reacting the intermediate of formula V with a compound of the formula $R_3$—NCS, wherein $R_3$ is as defined above. In this process, the intermediate of formula V and $R_3$—NCS are reacted in a protic solvent, such as methanol or ethanol, preferably ethanol, at a temperature ranging from about ambient temperature to 78° C., preferably at about the reflux of the solvent. The reaction is preferably carried out for about 12 to 24 hours but this period can be longer or shorter depending on the $R_3$ substituent to be added. When $R_3$ is 1- or 2-adamantyl, it is preferable to use a large excess of the reactant $R_3$—NCS and to let the reaction proceed for a period of about two days to a week. For cases in which the intermediate of formula VI is isolated prior to the formation of the intermediate of formula VI, a catalytic amount of potassium cyanide is added to the reaction mixture to catalyze the formation of the intermediate of formula VII.

In step 6, the intermediate of formula VII is reacted with a compound of the formula $R_4$—C(O)CH$_2$—X, wherein $R_4$ is as defined above and X is a leaving group, such as chloride or bromide, to provide the intermediate of formula VIII. In this process, the intermediate of formula VII is reacted with a strong base, such as sodium hydride, potassium tert-butoxide or potassium bis(trimethylsilyl)amide, preferably potassium bis(trimethylsilyl)amide, in a polar aprotic solvent such as THF, ethyl ether, dimethoxyethane (DME) or dimethylformamide (DMF), preferably THF, at a temperature ranging from about −78° C. to 35° C., preferably about 0° C. After stirring for about 30 minutes, the compound of formula $R_4$—C(O)CH$_2$—X is added to the reaction mixture and the mixture is then allowed to warm to ambient temperature. Alternatively, the intermediate of formula VII is reacted with the compound of formula $R_4$—C(O)CH$_2$—X in a polar solvent, such as THF, DMF, acetonitrile or acetone, preferably acetone, in the presence of an acid scavenger, such as carbonate or an organic tertiary amine, preferably potassium carbonate. The reaction temperature is maintained between about −78° C. to 140° C., preferably between about 0° C. to ambient temperature, to provide the intermediate of formula VIII.

In step 7, the compound of formula I is formed by treating the intermediate of formula VIII with a thiophile, such as triphenyl phosphine, tributyl phosphine or trimethylphosphite, preferably triphenyl phosphine, in a solvent such as toluene or benzene, preferably toluene, at a temperature ranging from about 25° C. to 120° C., preferably about 100° C.

The starting materials used in the process of Scheme 1 are either known in the literature or commercially available.

The compounds of formula I that are basic in nature are capable of forming a wide variety of different salts with various inorganic and organic acids. Although such salts must be pharmaceutically acceptable for administration to animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon evaporation of the solvent, the desired solid salt is readily obtained. The desired acid addition salt can also be precipitated from a solution of the free base in an organic solvent by adding to the solution an appropriate mineral or organic acid. Cationic salts of the compounds of formula I are similarly prepared except through reaction of a carboxy group, such as where $R_5$ is carboxy, with an appropriate cationic salt reagent such as sodium, potassium, calcium, magnesium, ammonium, N,N'-dibenzylethylenediamine, N-methylglucamine (meglumine), ethanolamine, tromethamine, or diethanolamine.

The compounds of formula I and their pharmaceutically acceptable salts (hereinafter referred to, collectively, as "the therapeutic compounds") can be administered orally, transdermally (e.g., through the use of a patch), parenterally or topically. Oral administration is preferred. In general, compounds of the formula I and their pharmaceutically acceptable salts are most desirably administered in dosages ranging from about 1.0 mg up to about 500 mg per day, preferably from about 1 to about 100 mg per day in single or divided (i.e., multiple) doses.

Compounds of the formula I and their pharmaceutically acceptable salts will ordinarily be administered in daily dosages ranging from about 0.01 to about 10 mg per kg body weight per day, in single or divided doses. Variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds may be administered alone or in combination with pharmaceutically acceptable carriers or diluents by either of the two routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art.

Additionally, it is also possible to administer the therapeutic compounds topically and this may preferably be done by way of creams, jellies, gels, pastes, ointments and the like, in accordance with standard pharmaceutical practice.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

The compounds of formula I exhibit activity as Ras farnesylation inhibitors and are useful in the treatment of cancer and the inhibition of abnormal cell growth in mammals, including humans. The activity of the compounds of formula I as Ras farnesylation inhibitors may be determined by their ability, relative to a control, to inhibit Ras farnesyl transferase in vitro. This procedure is described below.

A crude preparation of human farnesyl transferase (FTase) comprising the cytosolic fraction of homogenized brain tissue is used for screening compounds in a 96-well assay format. The cytosolic fraction is prepared by homogenizing approx. 40 grams fresh tissue in 100 ml of sucrose/$MgCl_2$/EDTA buffer (using a Dounce homogenizer; 10–15 strokes), centrifuging the homogenates at 1000 g for 10 minutes at 4° C., re-centrifuging the supernatant at 17,000 g for 15 minutes at 4° C., and then collecting the resulting supernatant. This supernatant is diluted to contain a final concentration of 50 mM Tris HCl (pH 7.5), 5 mM DTT, 0.2 M KCl, 20 $\mu$M $ZnCl_2$, 1 mM PMSF and re-centrifuged at 178,000 g for 90 minutes at 4° C. The supernatant, termed "crude FTase" was assayed for protein concentration, aliquoted, and stored at −70° C.

The assay used to measure in vitro inhibition of human FTase is a modification of the method described by Amersham LifeScience for using their Farnesyl transferase (3H) Scintillation Proximity Assay (SPA) kit (TRKQ 7010). FTase enzyme activity is determined in a volume of 100 $\mu$l containing 50 mM N-(2-hydroxy ethyl) piperazine-N'-(2-ethane sulfonic acid) (HEPES), pH 7.5, 30 mM $MgCl_2$, 20 $\mu$M KCl, 5 mM $Na_2HPO_4$, 5 mM dithiothreitol (DTT), 0.01% Triton X-100, 5% dimethyl sulfoxide (DMSO), 20 $\mu$g of crude FTase, 0.12 $\mu$M [3H]-farnesyl pyrophosphate ([3H]-FPP; 36000 dpm/pmole, Amersham LifeScience), and 0.2 $\mu$M of biotinylated Ras peptide KTKCVIS (Bt-KTKCVIS) that is N-terminally biotinylated at its alpha amino group and was synthesized and purified by HPLC in house. The reaction is initiated by addition of the enzyme and terminated by addition of EDTA (supplied as the STOP reagent in kit TRKQ 7010) following a 45 minute incubation at 37° C. Prenylated and unprenylated Bt-KTKCVIS is captured by adding 10 $\mu$l of streptavidin-coated SPA beads (TRKQ 7010) per well and incubating the reaction mixture for 30 minutes at room temperature. The amount of radioactivity bound to the SPA beads is determined using a MicroBeta 1450 plate counter. Under these assay conditions, the enzyme activity is linear with respect to the concentrations of the prenyl group acceptor, Bt-KTKCVIS, and crude FTase, but saturating with respect to the prenyl donor, FPP. The assay reaction time is also in the linear range.

The test compounds are routinely dissolved in 100% DMSO. Inhibition of farnesyl transferase activity is determined by calculating percent incorporation of tritiated-farnesyl in the presence of the test compound vs. its incorporation in control wells (absence of inhibitor). $IC_{50}$ values, that is, the concentration required to produce half maximal farnesylation of Bt-KTKCVIS, is determined from the dose-responses obtained.

The following Examples further illustrate the invention. In the following examples, "DMF" means dimethylformamide and "THF" means tetrahydrofuran.

EXAMPLE 1

4-{[5-Oxo-4,4-bis-pyridin-4-ylmethyl-1-(2,6,6-trimethyl-bicyclo[3.1.1]hept-3-ylmethyl)-imidazolidin-2-ylidene]-acetyl}-benzonitrile A. 2-Benzhydrylideneamino-3-pyridin-4-yl-propionic acid methyl ester.

Potassium bis(trimethylsilyl)amide (34.9 g, 175 mmol) was added under an atmosphere of dry $N_2$ to anhydrous THF (300 ml) and the resultant solution was cooled to −40° C. After the solution becomes homogeneous, 40.3 g (159 mmol) of methylbenzhydrylideneamino acetate was added and the resulting yellowish red solution was stirred at −40° C. After stirring for one hour, a solution of 21.0 g (165 mmol) of 4-picolyl chloride dissolved in anhydrous THF (50 ml) was added to the mixture. After the addition was complete, the reaction was warmed to ambient temperature and stirring was continued for 12 hours. The reaction was subsequently partitioned between ethyl acetate and brine. The aqueous layer was washed two times with ethyl acetate.

The ethyl acetate extracts were combined, dried over sodium sulfate ($Na_2SO4$), filtered and concentrated under vacuum to give a red oil. The product crystallized upon the addition of hexanes (30 ml). The solution was placed in the freezer to promote further crystallization. The product was collected via suction filtration and washed with hexanes. The filtrate was concentrated in vacuo and a second crop of crystals was obtained upon the addition of hexanes. The crystals from both crops were combined and dry under vacuum to give 44.4 g (129 mmol) of the desired tan solid.

B. 2-Benzhydrylideneamino-3-pyridin-4-yl-2-pyridin-4-ylmethyl-propionic acid methyl ester.

Potassium bis(trimethylsilyl)amide (28.2 g, 141 mmol) was added under an atmosphere of dry $N_2$ to anhydrous THF (290 ml) and the resultant solution was cooled to −40° C. After the solution becomes homogeneous, a solution of 44.3 g (129 mmol) 2-benzhydrylideneamino-3-pyridin-4-yl-propionic acid methyl ester dissolved in anhydrous THF (100 ml) was added dropwise to the reaction. After the addition was complete, the reaction was stirred at −40° C. After stirring for one hour, a solution of 18.5 g (145 mmol) of 4-picolyl chloride dissolved in anhydrous THF (40 ml) was added to the reaction. After the addition was complete, the reaction was warmed to ambient temperature and stirring was continued for 12 hours. The reaction mixture was subsequently partitioned between ethyl acetate and brine. The aqueous layer was washed two times with ethyl acetate. The ethyl acetate extracts were combined, dried over $Na_2SO_4$, filtered and concentrated under vacuum to a volume of 50 ml. The product precipitated upon the addition of hexanes (100 ml) to the reaction mixture. The product was collected via suction filtration, washed with hexanes, dried under vacuum to give 49.7 g (114 mmol) of the titled compound as an orange solid.

C. 2-Amino-3-pyridin-4-yl-2-pyridin-4-ylmethyl-propionic acid methyl ester

2-Benzhydrylideneamino-3-pyridin-4-yl-2-pyridin-4-ylmethyl-propionic acid methyl ester (49.6 g, 113 mmol) was dissolved in anhydrous THF (640 ml). To the reaction was added 227 ml of a solution of 2.0 M aqueous hydrochloric acid (HCl). The mixture was stirred at ambient temperature for one hour. The reaction was subsequently concentrated under vacuum to remove the THF. The reaction was then partitioned between ethyl ether and water. The aqueous layer was washed two more times with ethyl ether. The pH of the aqueous layer was then adjusted to 9 with sodium carbonate ($Na_2CO_3$) and the solution is extracted with methylene chloride until virtually no product is left in the methylene chloride ($CH_2Cl_2$) layer. The $CH_2Cl_2$ extracts were combined, dried over $Na_2SO_4$, filtered and concentrated under vacuum to give 25.6 g (94.4 mmol) of the titled compound as a yellow solid.

D. 5,5-Bis-pyridin-4-ylmethyl-2-thioxo-3-(2,6,6-trimethyl-bicyclo[3.1.1]hept-3-ylmethyl)-imidazolidin-4-one 2-Amino-3-pyridin-4-yl-2-pyridin-4-ylmethyl-propionic acid methyl ester (2.50 g, 9.23 mmol) was dissolved in absolute ethanol (50 ml). To the reaction was added 5.01 g (23.9 mmol) of (+)-3-pinanemethyl isothiocyanate. The reaction was then heated to 75° C. under an atmosphere of dry $N_2$. After stirring for 16 hours, the reaction was subsequently concentrated under vacuum. The resulting oil was chromatographed on silica gel using a gradient of neat ethyl acetate to 5% methanol in ethyl acetate to give 3.32 g (7.41 mmol) of the titled compound.

E. 4-{[5-Oxo-4,4-bis-pyridin-4-ylmethyl-1-(2,6,6-trimethyl-bicyclo[3.1.1]hept-3-ylmethyl)-imidazolidin-2-ylidene]-acetyl}-benzonitrile 5,5-Bis-pyridin-4-ylmethyl-2-thioxo-3-(2,6,6-trimethyl-bicyclo[3.1.1]hept-3-ylmethyl)-imidazolidin-4-one (101 mg, 0.225 mmol) was dissolved in anhydrous THF (3.0 ml) under an atmosphere of dry $N_2$. The reaction was then cooled to 0° C. and potassium bis(trimethylsilyl)amide (46.8 mg, 0.235 mmol) was added. After stirring for 15 minutes, 4-cyanophenacyl bromide (51.5 mg, 0.230 mmol) was added to the reaction and the reaction was subsequently stirred for 20 minutes. The mixture was subsequently partitioned between $CH_2Cl_2$ and saturated sodium bicarbonate ($NaHCO_3$) solution. The $CH_2Cl_2$ layer was dried over $Na_2SO_4$, filtered, and concentrated under vacuum to give a yellow oil. The oil was chromatographed on silica gel using 50% ethyl acetate in hexanes to remove unreacted 4-cyanophenacyl bromide and then eluted with 2% methanol in ethyl acetate to give 112 mg (0.189 mmol) of the titled compound as a yellow foam.

F. 4-{[5-Oxo-4,4-bis-pyridin-4-ylmethyl-1-(2,6,6-trimethyl-bicyclo[3.1.1]hept-3-ylmethyl)-imidazolidin-2-ylidene]-acetyl}-benzonitrile 4-{[5-Oxo-4,4-bis-pyridin-4-ylmethyl-1-(2,6,6-trimethyl-bicyclo[3.1.1]hept-3-ylmethyl)-imidazolidin-2-ylidene]-acetyl}-benzonitrile (110 mg, 0.186 mmol) was dissolved in anhydrous toluene (10 ml) under an atmosphere of $N_2$. To the reaction was added triphenylphosphine (200 mg, 0.763 mmol) followed by 10 μl of N-ethyldiisopropyl amine. The reaction was subsequently heated to 100° C. After stirring for 40 hours, the reaction was concentrated under vacuum and then partitioned between 0.001 N HCl and ethyl ether. The aqueous layer is washed two times with ethyl ether and subsequently basified to pH=8 with $NaHCO_3$. The product was then extracted into $CH_2Cl_2$, dried over $MgSO_4$, filtered and concentrated under vacuum to give 101 mg (0.181 mmol) of the titled compound as a tan foam: C.I. m/z 560 [M+1]; $^1$H NMR ($CDCl_3$)δ 10.41 (br s, 1H), 8.47 (m, 4H), 7.83 (d, J=8.4 Hz, 2H), 7.71 (d, J=8.4 Hz, 2H), 7.15 (m, 4H), 5.24 (s, 1H), 3.27 (d, J=13.3 Hz, 2H), 3.05–3.22 (m, 3H), 2.92 (dd, J=4.9, 13.9 Hz, 1H), 2.28 (m, 1H), 1.73 (m, 4H), 1.50 (m, 1H), 1.13 (s, 3H), 1.04 (m, 1H), 0.92 (dd, J=7.1 Hz, 3H), 0.82 (s, 3H), 0.63 (d, J=9.8 Hz, 1H).

EXAMPLE 2

3-tert-Butyl-2-(2-oxo-2-phenyl-ethylidene)-5,5-bis-pyridin-4-ylmethyl-imidazolidin-4-one The same procedure that was used in example 1 was followed except that tertbutylisothiocyanate was used in the place of (+)-3-pinanemethyl isothiocyanate in step D and bromoacetophenone was substituted for 4-cyanophenacyl bromide in step E to give the titled compound as a colorless oil: C.I. m/z 441 [M+1]; $^1$H NMR ($CDCl_3$)δ 11.63 (br s, 1H), 8.47 (d, J=8.5 Hz, 4H), 7.72 (d, J=8.3 Hz, 2H), 7.41 (d, J=8.3 Hz, 2H), 5.52 (s, 1H), 3.21 (d, J=13.2 Hz, 2H), 3.00 (d, J=13.2 Hz, 2H), 1.19 (s, 9H).

EXAMPLE 3

2-[2-(4-Bromo-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one The same procedure that was used in example 1 was followed except that 4-bromophenylacyl bromide was substituted for 4-cyanophenacyl bromide in step E to give the titled compound as a tan foam: C.I. m/z 613 M+1, 615 M+3; $^1$H NMR ($CDCl_3$)δ 10.34 (br s, 1H), 8.46 (m, 4H), 7.62 (d, J=8.6 Hz, 2H), 7.55 (d, J=8.6 Hz, 2H), 7.12 (m, 4H), 5.21 (s, 1H), 3.24 (d, J=13.3 Hz, 2H), 3.01–3.15 (m, 3H), 2.92 (dd, J=4.6, 13.8 Hz, 1H), 2.28 (m, 1H), 1.40–1.85 (m, 5H), 1.12

(s, 3H), 1.04 (m, 2H), 0.91 (d, J=7.1 Hz, 3H), 0.85 (d, J=9.7 Hz, 1H), 0.81 (s, 3H), 0.61 (d, J=9.7 Hz, 1H).

EXAMPLE 4

2-[2-(4-Chloro-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one The same procedure that was used in example 1 was followed except that 4-chlorophenylacyl bromide was substituted for 4-cyanophenacyl bromide in step E to give the titled compound as a tan foam: C.I. m/z M+1 569, M+3 571; $^1$H NMR (CDCl$_3$) δ 10.39 (br s, 1H), 8.46 (m, 4H), 7.70 (d, J=8.6 Hz, 2H), 7.39 (d, J=8.6 Hz, 2H), 7.12 (m, 4H), 5.22 (s, 1H), 3.24 (d, J=13.3 Hz, 2H), 3.01–3.16 (m, 3H), 2.91 (dd, J=4.6, 13.8 Hz, 1H), 2.28 (m, 1H), 1.50–1.80 (m, 5H), 1.12 (s, 3H), 1.05 (m, 2H), 0.91 (d, J=7.1 Hz, 3H), 0.84 (d, J=9.9 Hz, 1H), 0.81 (s, 3H), 0.61 (d, J=9.9 Hz, 1H).

EXAMPLE 5

2-[2-(3,4-Dichloro-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one The same procedure that was used in example 1 was followed except that 3,4-dichlorophenylacyl bromide was substituted for 4-cyanophenacyl bromide in step E to give the titled compound as a tan foam: C.I. m/z M+1 603, M+3 605, M+5 607; $^1$H NMR (CDCl$_3$)δ 10.36 (br s, 1H), 8.48 (m, 4H), 7.88 (s, 1H), 7.55 (d, J=8.5 Hz, 1H), 7.50 (d, J=8.5 Hz, 1H), 7.15 (m, 4H), 5.20 (s, 1H), 3.27 (d, J=13.3 Hz, 2H), 3.04–3.19 (m, 3H), 2.92 (dd, J=4.7, 13.7 Hz, 1H), 2.28 (m, 1H), 1.72 (m, 4H), 1.51 (m, 1H), 1.14 (s, 3H), 1.04 (m, 1H), 0.93 (d, J=7.1 Hz, 3H), 0.83 (s, 3H), 0.64 (d, J=9.9 Hz, 1H).

EXAMPLE 6

2-[2-(3-Nitro-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one The same procedure that was used in example 1 was followed except that 3-nitrophenylacyl bromide was substituted for 4-cyanophenacyl bromide in step E to give the titled compound as a tan foam: C.I. m/z 580 M+1; $^1$H NMR (CDCl$_3$)δ 10.40 (br s, 1H), 8.62 (m, 1H), 8.48 (m, 4H), 8.34 (dd, J=1.3, 7.6 Hz, 1H), 8.08 (dd, J=1.2, 7.6 Hz, 1H), 7.63 (t, J=8.0 , 1H) 7.15 (m, 4H), 5.30 (s, 1H), 3.29 (d, J=13.4 Hz, 2H), 3.07–3.23 (m, 3H), 2.94 (dd, J=4.7, 13.9 Hz, 1H), 2.32 (m, 1H), 1.75 (m, 4H), 1.53 (m, 1H), 1.14 (s, 3H), 1.05 (m, 2H), 0.98 (d, J=7.0 Hz, 3H), 0.84 (s, 3H), 0.65 (d, J=9.9 Hz, 1H).

EXAMPLE 7

2-[2-(4-Methoxy-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one The same procedure that was used in example 1 was followed except that 4-methoxyphenylacyl bromide was substituted for 4-cyanophenacyl bromide in step E to give the titled compound as a tan foam: C.I. m/z 565 M+1; $^1$H NMR (CDCl$_3$)δ 10.36 (br s, 1H), 8.47 (m, 4H), 7.77 (d, J=8.9 Hz, 2H), 7.15 (m, 4H), 6.95 (d, J=8.9 Hz, 2H), 5.26 (s, 1H), 3.87 (s, 3H), 3.24 (d, J=13.5 Hz, 2H), 3.01–3.18 (m, 3H), 2.91 (dd, J=4.8 Hz, 13.7 Hz, 1H), 2.26 (m, 1H), 1.72 (m, 4H), 1.51 (m, 1H), 1.14 (m, 3H), 1.05 (m, 2H), 0.93 (d, J=7.2 Hz, 3H), 0.83 (s, 3H), 0.64 (d, J=9.9 Hz, 1H).

EXAMPLE 8

2-[2-(3-Methoxy-phenyl)-2-oxo-ethylidene]-5,6-bis-pyridin-4-ylmethyl-3-(2,6,6-trimethyl-bicyclo[3.1.1]hept-3-ylmethyl)-imidazolidin-4-one The same procedure that was used in example 1 was followed except that 3-methoxyphenylacyl bromide was substituted for 4-cyanophenacyl bromide in step E to give the titled compound as a tan foam: C.I. m/z 565 M+1; $^1$H NMR (CDCl$_3$) δ 10.46 (br s, 1H), 8.46 (m, 4H),7.30–7.37 (m, 3H), 7.15 (m, 4H), 7.02 (m, 1H), 5.29 (s, 1H), 3.86 (s, 3H), 3.24 (d, J=13.3 Hz, 2H), 3.02–3.17 (m, 3H), 2.91 (dd, J=4.9, 13.9 Hz, 1H), 2.26 (m, 1H), 1.72 (m, 4H), 1.50 (m, 1H), 1.13 (s, 3H), 1.04 (m, 2H), 0.93 (d, J=7.1 Hz, 3H), 0.82 (s, 3H), 0.63 (d, J=9.8 Hz, 1H).

EXAMPLE 9

2-[2-(2-Methoxy-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one The same procedure that was used in example 1 was followed except that 2-methoxyphenylacyl bromide was substituted for 4-cyanophenacyl bromide in step E to give the titled compound as a tan foam: C.I. m/z 565 M+1; $^1$H NMR (CDCl$_3$)δ 10.39 (br s, 1H), 8.48 (m, 4H), 7.76 (dd, J=1.7, 7.4 Hz, 1H), 7.40 (m, 1H), 7.16 (m, 4H), 7.04 (m, 1H), 6.92 (d, J=8.0 Hz, 1H), 5.52 (s, 1H), 3.80 (s, 3H), 3.24 (d, J=13.3 Hz, 2H), 3.00–3.07 (m, 3H), 2.90 (dd, J=5.2, 13.7 Hz, 1H), 2.27 (m, 1H), 1.70–1.77 (m, 4H), 1.50 (m, 1H), 1.14 (s, 3H), 1.08 (m, 2H), 0.88 (d, J=7.3 Hz, 3H), 0.85 (s, 3H), 0.64 (d, J=9.8 Hz, 1H).

EXAMPLE 10

2-(2-Biphenyl-4-yl-2-oxo-ethylidene)-5,5-bis-pyridin-4-ylmethyl-3-(2,6,6-trimethyl-bicyclo[3.1.1]hept-3-ylmethyl)-imidazolidin-4-one The same procedure that was used in example 1 was followed except that 2-bromo-4'-phenylacetophenone was substituted for 4-cyanophenacyl bromide in step E to give the titled compound as a colorless oil: C.I. m/z 611 M+1; $^1$H NMR (CDCl$_3$)δ 10.42 (br s, 1H), 8.46 (m, 4H), 7.85 (d, J=8.5 Hz, 2H), 7.61–7.67 (m, 4H), 7.37–7.48 (m, 3H), 7.16 (m, 4H), 5.33 (s, 1H), 3.24 (d, J=13.2 Hz, 2H), 2.91–3.13 (m, 4H), 2.26 (m, 1H), 1.60–1.75 (m, 4H), 1.51 (m, 1H), 1.12 (s, 3H), 1.06 (m, 2H), 0.93 (d, J=7.1 Hz, 3H), 0.82 (s, 3H), 0.63 (d, J=9.9 Hz, 1H).

EXAMPLE 11

2-(2-Naphthalen-2-yl-2-oxo-ethylidene)-5,5-bis-pyridin-4-ylmethyl-3-(2,6,6-trimethyl-bicyclo[3.1.1]hept-3-ylmethyl)-imidazolidin-4-one The same procedure that was used in example 1 was followed except that 2-bromo-2'-acetonapthone was substituted for 4-cyanophenacyl bromide in step E to give the titled compound as a tan foam: C.I. m/z 585 M+1; $^1$H NMR (CDCl$_3$)δ 10.42 (br s, 1H), 8.46 (m, 4H), 8.27 (s, 1H), 7.87 (m, 4H), 7.53 (m, 3H), 7.17 (m, 4H), 5.45 (s, 1H), 3.25 (d,J=13.3 Hz, 2H), 3.04–3.16 (m, 3H), 2.96 (dd, J=4.9, 14.0 Hz, 1H), 2.26 (m, 1H), 1.72 (m, 4H), 1.53 (m, 1H), 1.13 (s, 3H), 1.07 (m, 2H), 0.97 (d, J=7.1 Hz, 3H), 0.82 (s, 3H), 0.64 (d,J=9.8 Hz, 1H).

EXAMPLE 12

2-[2-(4-Fluoro-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one The same procedure that was used in example 1 was followed except that 4-fluorophenacylbromide was substituted for 4-cyanophenacyl bromide in step E to give the titled compound as a tan foam: C.I. m/z 553 M+1; $^1$H NMR (CDCl$_3$)δ 10.37 (br s, 1H), 8.46 (m, 4H), 7.79 (dd, J=5.5, 8.9 Hz, 2H), 7.07–7.17 (m, 6H), 5.23 (s, 1H), 3.26 (d, J=13.4 Hz, 2H), 3.03–3.18 (m, 3H), 2.92 (dd, J=5.0, 13.7 Hz, 1H), 2.25 (m, 1H), 1.74 (m, 4H), 1.51 (m, 1H), 1.14 (s, 3H) 1.05 (m, 2H), 0.93 (d, J=7.2 Hz, 3H), 0.83 (s, 3H), 0.64 (d, J=9.8 Hz, 1H).

EXAMPLE 13

2-[2-(2,4-Difluoro-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one The same procedure that was used in example 1 was followed except that 2-chloro-2'-4-difluoroacetophenone was substituted for 4-cyanophenacyl bromide in step E to give the titled compound as a tan foam: C.I. m/z 571 M+1; $^1$H NMR (CDCl$_3$)δ 10.40 (br s, 1H), 8.48 (m, 4H), 7.95 (m, 1H), 7.14 (m, 4H), 6.97 (m, 1H), 6.81 (m, 1H), 5.38 (s, 1H), 3.25 (d, J=13.3 Hz, 2H), 3.02–3.19 (m, 3H), 2.89 (dd, J=4.9, 13.8 Hz, 1H), 2.26 (m, 1H), 1.69 (m, 4H), 1.52 (m, 1H), 1.14 (s, 3H), 1.03 (m, 2H), 0.91 (d, J=7.1 Hz, 3H), 0.83 (s, 3H), 0.64 (d, J=9.8 Hz, 1H).

EXAMPLE 14

4-{[1-(2,2-Dimethyl-propyl)-5-oxo-4,4-bis-pyridin-4-ylmethyl-imidazolidin-2-ylidene]-acetyl}-benzonitrile The same procedure that was used in example 1 was followed except that neopentylisothiocyanate was used in the place of (+)-3-pinanemethyl isothiocyanate in step D to give the titled compound as a foam: C.I. m/z 480 [M+1]; $^1$H NMR (CDCl$_3$)δ 10.73 (br s, 1H), 8.51 (m, 4H), 7.84 (d, J=8.4 Hz, 2H), 7.72 (d, J=8.4 Hz, 2H), 7.19 (m, 4H), 5.22 (s, 1H), 3.30 (d, J=13.3 Hz, 2H), 3.13 (d, J=13.3 Hz, 2H), 2.86 (s, 2H), 0.60(s, 9H).

EXAMPLE 15

4-{[1-(2-Adamantan-1-yl-ethyl)-5-oxo-4,4-bis-pyridin-4-ylmethyl-imidazolidin-2-ylidene]-acetyl}-benzonitrile A. 1-(2-isothiocyanato-ethyl)-adamantane 2-adamantan-1-yl-ethylamine (380 mg, 2.12 mmol) was dissolved in CH$_2$Cl$_2$ (10 ml) under a dry atmosphere of N$_2$. To this solution was added 1,1'-thiocarbonyl-diimidazole (420 mg, 2.12 mmol). After stirring at ambient temperature for 12 hours, the solution was partitioned between 0.1 N HCl and CH$_2$Cl$_2$. The CH$_2$Cl$_2$ layer was washed with water, then saturated NaHCO$_3$ solution and finally brine. The CH$_2$Cl$_2$ layer was dried over MgSO$_4$, filtered and concentrated under vacuum to give 417 mg of a yellow solid. The product was chromatographed on silica gel using hexanes to give 125 mg of the titled compound as a white solid: $^1$H NMR (CDCl$_3$)δ 3.52 (m, 2H), 1.98 (br s, 3H), 1.49–1.76 (m, 17H).

B. 4-{[1-(2-Adamantan-1-yl-ethyl)-5-oxo-4,4-bis-pyridin-4-ylmethyl-imidazolidin-2-ylidene]-acetyl}-benzonitrile The same procedure that was used in example 1 was followed except that 1-(2-isothiocyanato-ethyl)-adamantane was used in the place of (+)-3-pinanemethyl isothiocyanate in step D to give the titled compound as a foam: C.I. m/z 572 [M+1]; $^1$H NMR (CDCl$_3$)δ 10.38 (br s, 1H), 8.48 (m, 4H), 7.82 (d, J=8.3 Hz, 2H), 7.71 (d, J=8.3 Hz, 2H), 7.15 (m, 4H), 5.11 (s, 1H), 3.30 (d, J=13.3 Hz, 2H), 3.00–3.19 (m, 4H), 0.50–2.0 (m, 17H).

EXAMPLE 16

4-{[5-Oxo-4,4-bis-pyridin-4-ylmethyl-1-(2,6,6-trimethyl-bicyclo[3.1.1]hept-3-yl)-imidazolidin-2-ylidene]-acetyl)-benzonitrile The same procedure that was used in example 1 was followed except that (1R,2R,3R,5S)-(−)-isopinocamphenylisothiocyanate was used in place of (+)-3-pinanemethyl isothiocyanate in step D to give the titled compound as a foam. (1R,2R,3R,5S)-(−)-isopinocamphenylisothiocyanate was prepared using (1R, 2R,3R,5S)-(−)-isopinocamphenylamine in the place of 2-adamantan-1-yl-ethylamine in step A of example 15: C.I. m/z 546 [M+1]; $^1$H NMR (CDCl$_3$)δ 10.93 (br s, 1H), 8.46 (m, 4H), 7.84 (d, J=8.3 Hz, 2H), 7.73 (d, J=8.3 Hz, 2H), 7.18 (m, 4H), 3.06–3.36 (m, 5H), 1.6–2.5 (m, 7H), 1.22 (s, 3H), 0.97 (s, 3H), 0.41 (d, J=7.0 Hz, 3H).

EXAMPLE 17

3-Cyclohexyl-2-(2-oxo-2-phenyl-ethylidene)-5,5-bis-pyridin-4-ylmethyl-imidazolidin-4-one The same procedure that was used in example 1 was followed except that cyclohexylisothiocyanate was used in the place of (+)-3-pinanemethyl isothiocyanate in step D and bromoacetophenone was substituted for 4-cyanophenacyl bromide in step E to give the titled compound as a foam: C.I. m/z 467 [M+1]; $^1$H NMR (CDCl$_3$)δ 10.72 (br s, 1H), 8.45 (m, 4H), 7.76 (m, 2H), 7.33–7.49 (m, 3H), 7.13 (m, 4H), 5.26 (s, 1H), 3.24 (d, J=13.2 Hz, 2H), 3.17 (m, 1H), 3.02 (d, J=13.2 Hz, 2H), 0.70–1.70 (m, 10H).

EXAMPLE 18

2-[2-(4-Nitro-phenyl)-2-oxo-ethylidene]-6,5-bis-pyridin-4-ylmethyl-3-(2,6,6-trimethyl-bicyclo[3.1.1]hept-3-ylmethyl)-imidazolidin-4-one The same procedure that was used in example 1 was followed except that α-bromo-p-nitroacetophenone was substituted for 4-cyanophenacyl bromide in step E to give the titled compound as a foam: C.I. m/z 580 [M+1]; $^1$H NMR (CDCl$_3$)δ 10.83 (br s, 1H), 8.48 (m, 4H), 8.28 (d, J=8.7 Hz, 2H), 7.90 (d, J=8.7 Hz, 2H), 5.27 (s, 1H), 3.29 (d, J=13.3 Hz, 2H), 3.05– 3.20 (m, 3H), 2.95 (dd, J=4.8, 13.9 Hz, 1H), 2.29 (m, 1H), 1.75 (m, 4H), 1.52 (m, 1H), 1.15 (s, 3H), 1.06 (m, 1H), 0.94 (d, J=7.1 Hz, 3H), 0.83 (s, 3H), 0.64 (d, J=9.9 Hz, 1H).

EXAMPLE 19

2-[2-Oxo-2-phenyl-ethylidene]-5,5-bis-pyridin-4-ylmethyl-3-(2,6,6-trimethyl-bicyclo[3.1.1]hept-3-ylmethyl)-imidazolidin-4-one The same procedure that was used in example 1 was followed except that bromoacetophenone was substituted for 4-cyanophenacyl bromide in step E to give the titled compound as a foam: C.I. m/z 535 [M+1]; $^1$H NMR (CDCl$_3$)δ 10.72 (br s, 1H), 8.47 (m, 4H), 7.78 (m, 2H), 7.40–7.53 (m, 3H), 7.15 (m, 4H), 5.31 (s, 1H), 3.24 (d, J=13.3 Hz, 2H), 3.03-3.18 (m, 3H), 2.93 (dd, J=5.0, 13.9 Hz, 1H), 2.27 (m, 1H), 1.74 (m, 4H), 1.51 (m, 1H), 1.14 (s, 3H), 1.04 (m, 1H), 0.96 (d, J=8.0 Hz, 3H), 0.83 (s, 3H), 0.64 (d,J=9.8 Hz, 1H).

EXAMPLE 20

2-[2-Oxo-2-phenyl-ethylidene]-5,5-bis-pyridin-4-ylmethyl-3-(2,6,6-trimethyl-bicyclo[3.1.1]hept-3-ylmethyl)-imidazolidin-4-one (Enantiomer of example 19)

The same procedure that was used in example 1 was followed except that bromoacetophenone was substituted for 4-cyanophenacyl bromide in step E and (−)-3-pinanemethyl isothiocyanate was used in the place of (+)-3-pinanemethyl isothiocyanate in step D to give the titled compound as a foam: C.I. m/z 535 [M+1]; $^1$H NMR (CDCl$_3$)δ 10.72 (br s, 1H), 8.47 (m, 4H), 7.78 (m, 2H), 7.40–7.53 (m, 3H), 7.15 (m, 4H), 5.31 (s, 1H), 3.24 (d, J=13.3 Hz, 2H), 3.03–3.18 (m, 3H), 2.93 (dd, J=5.0, 13.9 Hz, 1H), 2.27 (m, 1H), 1.74 (m, 4H), 1.51 (m, 1H), 1.14 (s, 3H), 1.04 (m, 1H), 0.96 (d, J=8.0 Hz, 3H), 0.83 (s, 3H), 0.64 (d, J=9.8 Hz, 1H).

EXAMPLE 21

2-{2-Oxo-2-[4-(2H-tetrazol-5-yl)-phenyl]-ethylidene}-5,5-bis-pyridin-4-ylmethyl-3-(2,6,6-trimethyl-bicyclo[3.1.1]hept-3-ylmethyl)-imidazolidin-4-one 4-{[5-Oxo-4,4-bis-pyridin-4-ylmethyl-1-(2,6,6-trimethyl-bicyclo[3.1.1]hept-3-ylmethyl) imidazolidin-2-ylidene]-acetyl}-benzonitrile (31.0 mg, 0.055 mmol), which was prepared via the procedure outlined in example 1, was dissolved in xylenes (1.0 ml) under an atmosphere of dry N$_2$. To the reaction was added azidotrimethyltin (23.4 mg, 0.114 mmol) and the reaction was then heated to 130° C. After stirring for 12 hours, the reaction was concentrated under vacuum and to the resulting residue was added a 1:1 solution of 0.5 N HCl and CH$_2$Cl$_2$ (1.0 ml). The reaction was then stirred for 2 hours at ambient temperature. The reaction was then partitioned between water and CH$_2$Cl$_2$. The aqueous layer was washed with CH$_2$Cl$_2$, basified to pH=6 with NaHCO$_3$ and extracted three times with CH$_2$Cl$_2$. The CH$_2$Cl$_2$ layers were combined, dried over Na$_2$SO$_4$, filtered and concentrated under vacuum to give 30 mg of the titled compound as a white solid: C.I. m/z 603 [M+1]; $^1$H NMR (CDCl$_3$)δ 10.55 (br s, 1H), 8.45 (m, 4H), 8.21 (d, J=8.0 Hz, 2H), 7.83 (d, J=8.0 Hz, 2H), 7.17 (m, 4H), 5.28 (s, 1H), 3.27 (d, J=13.2 Hz, 2H), 3.07–3.20 (m, 3H), 2.93 (dd, J=4.9, 13.9 Hz, 1H), 2.28 (m, 1H), 1.73 (m, 4H), 1.50 (m, 1H), 1.11 (s, 3H), 1.04 (m, 1H), 0.92 (d, J=6.6 Hz, 1H), 0.83 (s, 3H), 0.63 (d, J=9.8 Hz, 1H).

EXAMPLE 22

4-[(1-Adamant-1-ylmethyl-5-Oxo-4,4-bis-pyridin-4-ylmethyl-imidazolidin-2-ylidene)-acetyl]-benzonitrile The same procedure that was used in example 1 was followed except that 1-isothiocyanatomethyl-adamantane was used in place of (+)-3-pinanemethyl isothiocyanate in step D to give the titled compound as a foam. 1-Isothiocyanatomethyl-adamantane was prepared using 1-adamantanemethylamine in the place of 2-adamantan-1-yl-ethylamine in step A of example 15: C.I. m/z 558 [M+1]; $^1$H NMR (CDCl$_3$)δ 10.40 (br s, 1H), 8.48 (m, 4H), 7.85 (d, J=8.4 Hz, 2H), 7.73 (d, J=8.4 Hz, 2H), 7.14 (m, 4H), 5.22 (s, 1H), 3.27 (d, J=13.3 Hz, 2H), 3.10 (d, J=13.3 Hz, 2H), 2.72 (s, 2H), 0.60–1.90 (m, 15H)

EXAMPLE 23

4-[(1-Cyclohexylmethyl-5-Oxo-4,4-bis-pyridin-4-ylmethyl-imidazoldin-2-ylidene)-acetyl]-benzonitrile The same procedure that was used in example 1 was followed except that 1-isothiocyanatomethyl-cyclohexane was used in place of (+)-3-pinanemethyl isothiocyanate in step D to give the titled compound as a foam. 1-isothiocyanatomethyl-cyclohexane was prepared using cyclohexylmethylamine in the place of 2-adamantan-1-yl-ethylamine in step A of example 15: C.I. m/z 506 [M+1]; $^1$H NMR (CDCl$_3$)δ 10.32 (br s, 1H), 8.45 (m, 4H), 7.85 (d, J=8.4 Hz, 2H), 7.71 (d, J=8.4 Hz, 2H), 7.11 (m, 4H), 5.14 (s, 1H), 3.27 (d, J=13.3 Hz, 2H), 3.06 (d, J=13.3 Hz, 2H), 2.89 (d, J=7.3 Hz, 2H), 0.5–1.65 (m, 11H).

EXAMPLE 24

4-{[1-(6,6-Dimethyl-bicyclo[3.1.1]hept-2-ylmethyl)-5-Oxo-4,4-bis-pyridin-4-ylmethyl-imidazolidin-2-ylidene]-acetyl}-benzonitrile The same procedure that was used in example 1 was followed except that cis-myrtanylisothiocyanate was used in the place of (+)-3-pinanemethyl isothiocyanate in step D to give the titled compound as a foam. cis-Myrtanylisothiocyanate was prepared using (−)-cis-myrtanylamine in the place of 2-adamantan-1-yl-ethylamine in step A of example 15: C.I. m/z 546 [M+1]; $^1$H NMR (CDCl$_3$)δ 10.41 (br s, 1H), 8.47 (m, 4H), 7.85 (d, J=8.5 Hz, 2H), 7.72 (d, J=8.5 Hz, 2H), 7.13 (m, 4H), 5.14 (s, 1H), 3.26 (d, J=13.3 Hz, 2H), 3.04–3.13 (m, 4H), 2.20 (m, 1H), 1.07–1.90 (m, 6H), 1.06 (s, 3H), 1.03 (s, 3H), 0.97 (m, 1H), 0.62 (d, J=9.9 Hz, 1H).

EXAMPLE 25

3-Hexyl-2-(2-oxo-2-phenyl-ethylidene)-5,5-bis-pyridin-4-ylmethyl-imidazolidin-4-one The same procedure that was used in example 1 was followed except that bromoacetophenone was substituted for 4-cyanophenacyl bromide in step E and hexyl isothiocyanate was used in the place of (+)-3-pinanemethyl isothiocyanate in step D to give the titled compound as a foam: C.I. m/z 469 [M+1]; $^1$H NMR (CDCl$_3$)δ 10.82 (br s, 1H), 8.45 (m, 4H), 7.76 (d, J=8.2 Hz, 2H), 7.43 (m, 3H), 7.12 (m, 4H), 5.18 (s, 1H), 3.22 (d, J=13.3 Hz, 2H), 3.04 (m, 4H), 0.82–1.30 (m, 11H).

EXAMPLE 26

3-Napthalen-1-yl-2-(2-oxo-2-phenyl-ethylidene)-5,5-bis-pyridin-4-ylmethyl-imidazolidin-4-one The same procedure that was used in example 1 was followed except that bromoacetophenone was substituted for 4-cyanophenacyl bromide in step E and 1-naphthyl isothiocyanate was used in the place of (+)-3-pinanemethyl isothiocyanate in step D to give the titled compound as a foam: C.I. m/z 511 [M+1]; $^1$H NMR (CDCl$_3$)δ 8.59 (m, 4H), 7.85 (d, J=8.3 Hz, 1H), 7.79 (d, J=8.3 Hz, 1H), 7.48 (d, J=7.3 Hz, 2H), 7.18–7.43 (m, 11H), 6.24 (d, J=7.3 Hz, 1H), 5.68 (d, J=8.3 Hz, 1H), 4.61 (s, 1H), 3.45 (d, J=13.3 Hz, 2H), 3.29 (d, J=13.3 Hz, 2H).

EXAMPLE 27

3-Adamantan-1-yl-2-(2-oxo-2-phenyl-ethylidene)-5,5-bis-pyridin-4-ylmethyl-imidazolidin-4-one The same procedure that was used in example 1 was followed except that bromoacetophenone was substituted for 4-cyanophenacyl bromide in step E and 1-adamantyl isothiocyanate was used in the place of (+)-3-pinanemethyl isothiocyanate in step D to give the titled compound as a tan solid: $^1$H NMR (CDCl$_3$)δ 11.91 (br s, 1H), 8.48 (m, 4H), 7.72 (m, 2H), 7.39–7.50 (m, 3H), 7.14 (m, 4H), 5.68 (s, 1H), 3.22 (d, J=13.3 Hz, 2H), 2.99 (d, J=13.3 Hz, 2H), 2.01 (br s, 3H), 1.90 (br s, 6H), 1.50–1.63 (m, 6H).

EXAMPLE 28

3-Adamantan-1-yl-2-[2-(4-nitro-phenyl)-2-oxo-ethylidene]-5,5-bis-pyridin-4-ylmethyl-imidazolidin-4-one The same procedure that was used in example 1 was followed except that α-bromo-p-nitroacetophenone was substituted for 4-cyanophenacyl bromide in step E and 1-adamantyl isothiocyanate was used in the place of (+)-3- pinanemethyl isothiocyanate in step D to give the titled compound as a tan solid: $^1$H NMR (CDCl$_3$)δ 10.44 (br s, 1H), 8.49 (m, 4H), 8.29 (d, J=8.7 Hz, 2H), 7.86 (d, J=8.7 Hz, 2H), 7.12 (m, 4H), 5.67 (s, 1H), 3.24 (d, J=13.3 Hz, 2H), 3.03 (d, J=13.3 Hz, 2H), 1.98 (br s, 3H), 1.83 (br s, 6H), 1.55 (br s, 6H).

EXAMPLE 29

4-[(1-Benzyl-5-Oxo-4,4-bis-pyridin-4-ylmethyl-imidazolid in-2-ylidene)-acetyl]-benzonitrile The same procedure that was used in example 1 was followed except that benzyl isothiocyanate was used in the place of (+)-3-pinanemethyl isothiocyanate in step D to give the titled compound as a tan foam: C.I. m/z 500 [M+1]; $^1$H NMR (CDCl$_3$)δ 10.73 (br s, 1H), 8.50 (m, 4H), 7.71 (d, J=8.4 Hz, 2H), 7.65 (d, J=8.4 Hz, 2H), 7.07–7.20 (m, 7H), 6.41 (d, J=7.6 Hz, 2H), 5.07 (s, 1H), 4.31 (s, 2H), 3.34 (d, J=13.3 Hz, 2H), 3.12 (d, J=13.3 Hz, 2H).

EXAMPLE 30

3-{[5-Oxo-4,4-bis-pyridin-4-ylmethyl-1-(2,6,6-trimethyl-bicyclo[3.1.1]hept-3-ylmethyl)-imidazolidin-2-ylidene]-acetyl}-benzonitrile The same procedure that was used in example 1 was followed except that 3-bromoacetyl-benzonitrile was substituted for 4-cyanophenacyl bromide in step E to give the titled compound as a tan solid: C.I. m/z 560 [M+1]; $^1$H NMR (CDCl$_3$)δ 10.38 (br s, 1H), 8.48 (m, 4H), 8.10 (t, J=1.4 Hz, 1H), 7.95 (dt, J=1.4, 8.0 Hz, 1H), 7.76 (dt, J=1.3, 7.9 Hz, 1H), 7.53 (t, J=7.8 Hz, 1H), 7.12 (m, 4H), 5.22 (s, 1H), 3.29 (d, J=13.3 Hz, 2H), 3.05–3.29 (m, 3H), 2.96 (dd, J=4.9, 13.9 Hz, 1H), 2.31 (m, 1H), 1.72 (m, 4H), 1.50 (m, 1H), 1.13 (s, 3H), 1.02 (m, 1H), 0.92 (d, J=7.2 Hz, 3H), 0.86 (s, 3H), 0.61 (d, J=9.8 Hz, 1H).

EXAMPLE 31

4-{[5-Oxo-4,4-bis-pyridin-4-ylmethyl-1-(2,6,6-trimethyl-bicyclo[3.1.1] hept-3-ylmethyl)-imidazolidin-2-ylidene]-acetyl}-benzoic acid ethyl ester A. 4-Bromoacetyl-benzoic acid ethyl ester Copper(II) bromide (2.47 g, 10.9 mmol) was suspended in ethyl acetate (7.5 ml) and the solution was subsequently heated to reflux. To the reaction was added a solution of 4-acetyl-benzoic acid ethyl ester (960.8 mg, 5.00 mmol) in chloroform (20 ml). After the mixture had stirred at reflux for 24 hours, the precipitate was removed via suction filtration and the resulting filtrate was partitioned between ethyl acetate and saturated NaHCO$_3$ solution. The ethyl acetate layer was dried over MgSO$_4$, filtered and concentrated under vacuum to give the titled compound as a white solid: $^1$H NMR (CDCl$_3$)δ 8.13 (m, 2H), 8.01 (m, 2H), 4.45 (s, 2H), 4.39 (q, J=7.2 Hz, 2H), 1.40 (t, J=7.2 Hz, 3H).

B. 4-{[5-Oxo-4,4-bis-pyridin-4-ylmethyl-1-(2,6,6-trimethyl-bicyclo[3.1.1]hept-3-ylmethyl)-imidazolidin-2-ylidene]-acetyl}-benzoic acid ethyl ester The same procedure that was used in example 1 was followed except that 4-bromoacetyl-benzoic acid ethyl ester was substituted for 4-cyanophenacyl bromide in step E to give the titled compound as a tan solid: $^1$H NMR (CDCl$_3$)δ 10.47 (br s, 1H), 8.49 (m, 4H), 8.11 (d, J=8.4 Hz, 2H), 7.82 (d, J=8.4 Hz, 2H), 7.16 (m, 4H), 5.30 (s, 1H), 4.40 (q, J=7.2 Hz, 2H), 3.25 (d, J=13.3 Hz, 2H), 3.02–3.21 (m, 3H), 2.92 (dd, J=4.9, 13.9 Hz, 1H), 2.29 (m, 1H), 1.71 (m, 4H), 1.51 (m, 1H), 1.41 (t, J=7.2 Hz, 3H), 1.14 (s, 3H), 1.05 (m, 1H), 0.92 (dd, J=7.1 Hz, 3H), 0.83 (s, 3H), 0.64 (d, J=9.8 Hz, 1H).

EXAMPLE 32

2-[2-Oxo-2-(4-trifluoromethyl-phenyl)-ethylidene]-5,5-bis-pyridin-4-ylmethyl-3-(2,6,6-trimethyl-bicyclo[3.1.1] hept-3-ylmethyl)-imidazolidin-4-one The same procedure that was used in example 1 was followed except that 2-bromo-1-(4-trifluoromethyl-phenyl)-ethanone was substituted for 4-cyanophenacyl bromide in step E to give the titled compound as a tan solid: $^1$H NMR (CDCl$_3$)δ 10.40 (br s, 1H), 8.46 (m, 4H), 7.86 (d, J=7.9 Hz, 2H), 7.70 (d, J=7.9 Hz, 2H), 7.14 (m, 4H), 5.27 (s, 1H), 3.26 (d, J=13.3 Hz, 2H), 3.04–3.19 (m, 3H), 2.93 (dd, J=4.9, 13.9 Hz, 1H), 2.27 (m, 1H), 1.73 (m, 4H), 1.51 (m, 1H), 1.13 (s, 3H), 1.05 (m, 1H), 0.93 (dd, J=7.2 Hz, 3H), 0.82 (s, 3H), 0.63 (d, J=9.9 Hz, 1H).

EXAMPLE 33

2-[2-(4-Methanesulphonyl-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one The same procedure was used in example 1 was followed except that 2-bromo-1-(4-methanesulphonyl-phenyl)-ethanone was substituted for 4-cyanophenacyl bromide in step E to give the titled compound as tan solid: C.I. m/z 613 [M+1]; $^1$H NMR (CDCl$_3$)δ 10.45 (br s, 1H), 8.46 (m, 4H), 8.01 (d, J=8.5 Hz, 2H), 7.95 (d, J=8.5 Hz, 2H), 7.13 (m, 4H), 5.25 (s, 1H), 3.27 (d, J=13.3 Hz, 2H), 2.88–3.18 (m, 7H), 2.27 (m, 1H), 1.72 (m, 4H), 1.50 (m, 1H), 1.13 (s, 3H), 1.04 (m, 1H), 0.91 (dd, J=7.1 Hz, 3H), 0.81 (s, 3H), 0.62 (d, J=9.8 Hz, I H).

EXAMPLE 34

4-[(1-Allyl-5-Oxo-4,4-bis-pyridin-4-ylmethyl-imidazolid in-2-ylidene)-acetyl]-benzonitrile The same procedure that was used in example 1 was followed except that allylisothiocyanate was used in the place of (+)-3-pinanemethyl isothiocyanate in step D to give the titled compound as an oil: C.I. m/z 450 [M+1]; $^1$H NMR (CDCl$_3$)δ 10.39 (br s, 1H), 8.45 (d,J=6.0 Hz, 4H), 7.80 (d, J=8.5 Hz, 2H), 7.68 (d, J=8.5 Hz, 2H), 7.11 (d,J=6.0 Hz, 4H), 5.28 (s, 1H), 5.10 (m, 1H), 4.90 (d, J=8.9 Hz, 1H), 4.40 (d, J=17.0 Hz, 1H), 3.73 (dd, J=1.6, 3.6 Hz, 2H), 3.31 (d, J=13.3 Hz, 2H), 3.10 (d, J=13.3 Hz, 2H).

EXAMPLE 35

4-[(1-Methyl-5-Oxo-4,4-bis-pyridin-4-ylmethyl-imidazolid in-2-ylidene)-acetyl]-benzonitrile The same procedure that was used in example 1 was followed except that methyl isothiocyanate was used in the place of (+)-3-pinanemethyl isothiocyanate in step D to give the titled compound as a tan solid: C.I. m/z 424.2 [M+1]; $^1$H NMR (CDCl$_3$)δ 10.36 (br s, 1H), 8.46 (d,J=6.1 Hz, 4H), 7.82 (d, J=8.5 Hz, 2H), 7.67 (d, J=8.5 Hz, 2H), 7.10 (d,J=6.1 Hz, 4H), 5.10 (s, 1H), 3.28 (d, J=13.3 Hz, 2H), 3.05 (d, J=13.3 Hz, 2H), 2.63 (s, 3H).

EXAMPLE 36

4-{[1-(2,2-Diethoxy-ethyl)-5-Oxo-4,4-bis-pyridin-4-ylmethyl-imidazolidin-2-ylidene]-acetyl}-benzonitrile The same procedure that was used in example 1 was followed except that 1,1-diethoxy-2-isothiocyanato-ethane was used in the place of (+)-3-pinanemethyl isothiocyanate in step D to give the titled compound as a tan solid: C.I. m/z 424.2 [M+1]; $^1$H NMR (CDCl$_3$)δ 10.38 (br s, 1H), 8.49 (d,J=6.0 Hz, 4H), 7.78 (d, J=8.5 Hz, 2H), 7.70 (d, J=8.5 Hz, 2H), 7.12 (d, J=6.0 Hz, 4H), 5.51 (s, 1H), 3.90 (t, J=5.2 Hz, 1H), 3.49 (m, 2H), 3.02–3.32 (m, 8H), 1.05 (t, J=7.1 Hz, 3H).

EXAMPLE 37

4-[(1-Adamantan-2-ylmethyl-5-Oxo-4,4-bis-pyridin-4-ylmethyl-imidazolidin-2-ylidene)-acetyl]-benzonitrile The same procedure that was used in example 1 was followed except that 2-isthiocyanatomethyl-adamantane was used in the place of (+)-3-pinanemethyl isothiocyanate in step D to give the titled compound as a tan solid. 2-isothiocyanatomethyl-adamantane was prepared using C-adamantan-2-yl-methylamine in the place of 2-adamantan-1-yl-ethylamine in step A of example 15: C.I. m/z 558.3 [M+1]; $^1$H NMR (CDCl$_3$)δ 10.49 (br s, 1H), 8.47 (d, J=5.8 Hz, 4H), 7.82 (d, J=8.2 Hz, 2H), 7.71 (d, J=8.2 Hz, 2H), 7.12 (d, J=5.8 Hz, 4H), 5.16 (s, 1H), 3.26 (d, J=13.4 Hz, 2H), 3.19 (d, J=7.3 Hz, 2H), 3.08 (d, J=13.4 Hz, 2H), 1.00–1.80 (m, 15H).

EXAMPLE 38

4-[(1-Adamantan-2-yl-5-Oxo-4,4-bis-pyridin-4-ylmethyl-imidazolidin-2-ylidene)-acetyl]-benzonitrile The same procedure that was used in example 1 was followed except that 2-isothiocyanato-adamantane was used in the place of (+)-3-pinanemethyl isothiocyanate in step D to give the titled compound as a tan solid: C.I. m/z 544.2 [M+1]; $^1$H NMR (CDCl$_3$)δ 10.93 (br s, 1H), 8.44 (d, J=6.0 Hz, 4H), 7.78 (d, J=8.3 Hz, 2H), 7.70 (d, J=8.3 Hz, 2H), 7.14 (d, J=6.0 Hz, 4H), 5.03 (s, 1H), 3.26 (d, J=13.3 Hz, 2H), 3.17 (m, 1H), 3.04 (d, J=13.3 Hz, 2H), 1.42–2.00 (m, 15H).

EXAMPLE 39

4-[(1-Bicyclo[2.2.2]oct-1-ylmethyl-5-Oxo-4,4-bis-pyridin-4-ylmethyl-imidazolid in-2-ylidene)-acetyl]-benzonitrile The same procedure that was used in example 1 was followed except that 1-isothiocyanatomethyl-bicyclo[2.2.2] octane was used in the place of (+)-3-pinanemethyl isothiocyanate in step D to give the titled compound as a tan solid. 1-isothiocyanatomethyl-bicyclo[2.2.2]octane was prepared by using C-bicyclo[2.2.2]oct-1-yl-methylamine in the place of 2-adamantan-1-yl-ethylamine in step A of example 15: C.I. m/z 532.2 [M+1]; $^1$H NMR (CDCl$_3$)δ 10.71 (br s, 1H), 8.46 (d, J=5.9 Hz, 4H), 7.84 (d, J=8.1 Hz, 2H), 7.71 (d, J=8.1 Hz, 2H), 7.14 (d,J=5.9 Hz, 4H), 5.17 (s, 1H), 3.25 (d, J=13.3 Hz, 2H), 3.10 (d, J=13.3 Hz, 2H), 2.73 (s, 2H), 1.34 (m, 7H), 0.86 (m, 6H).

EXAMPLE 40

4-[(5-Oxo-1-phenyl-4,4-bis-pyridin-4-ylmethyl-imidazolidin-2-ylidene)-acetyl]-benzonitrile The same procedure that was used in example 1 was followed except that phenyl isothiocyanate was used in the place of (+)-3-pinanemethyl isothiocyanate in step D to give the titled compound as a tan solid: $^1$H NMR (CDCl$_3$)δ 10.42 (br s, 1H), 8.56 (d, J=6.0 Hz, 4H), 7.70 (d, J=8.3 Hz, 2H), 7.62 (d, J=8.3 Hz, 2H), 7.23–7.44 (m, 3H), 7.22 (d, J=6.0 Hz, 4H), 6.40 (d, J=7.0 Hz, 2H), 4.82(s, 1H), 3.41 (d, J=13.3 Hz, 2H), 3.18 (d, J=13.3 Hz, 2H).

EXAMPLE 41

4-{[4-tert-Butyl-phenyl-5-oxo-4,4-bis-pyridin-4-ylmethyl-imidazolid in-2-ylidene)-acetyl]-benzonitrile The same procedure that was used in example 1 was followed except that 4-tert-butylphenyl isothiocyanate was used in the place of (+)-3-pinanemethyl isothiocyanate in step D to give the titled compound as a tan solid: $^1$H NMR (CDCl$_3$) 8 10.42 (br s, 1H), 8.52 (d, J=5.9 Hz, 4H), 7.70 (d, J=7.8 Hz, 2H), 7.61 (d, J=7.8 Hz, 2H), 7.36 (d, J=6.8 Hz, 2H), 7.21 (d,J=5.9 Hz, 4H), 6.30 (d, J=6.8 Hz, 2H), 4.86 (s, 1H), 3.41 (d, J=13.3 Hz, 2H), 3.18 (d, J=13.3 Hz, 2H), 1.30 (s, 9H).

EXAMPLE 42

4-{[1-(2-Ethyl-6,6-dimethyl-bicyclo[3.1.1]hept-3-ylmethyl)-5-Oxo-4,4-bis-pyridin 4-ylmethyl-imidazolidin-2-ylidene]-acetyl}-benzonitrile A. 2-Acetyl-6,6-dimethyl-bicyclo[3.1.1]heptane-3-carbonitrile 3-(3-Ethyl-2,2-dimethyl-cyclobutyl)-but-3-en-2-one (568 mg, 3.46 mmol) was dissolved in benzene (20 ml) under an atmosphere of dry N$_2$. To the solution was added a 1.0 M solution of diethylaluminum cyanide (5.0 ml) in toluene. After stirring at ambient temperature for 30 minutes, a 10% aqueous solution of potassium sodium tartrate (20 ml) was added to the reaction. After stirring at ambient temperature for 30 minutes, the reaction was partitioned between CH$_2$Cl$_2$ and 0.1 N aqueous sodium hydroxide (NaOH). The CH$_2$Cl$_2$ layer was washed with brine, dried over MgSO$_4$, filtered and concentrated under vacuum to give 551 mg of the titled compound as an oil: $^1$H NMR (CDCl$_3$)δ 3.99 (dt, J=4.3, 11.0 Hz, 1H), 3.14 (dd, J=3.1, 4.6 Hz, 1H), 2.62 (m, 1H), 2.53 (m, 1H), 2.41 (m, 1H), 2.22 (m, 1H), 2.17 (s, 3H), 2.01 (m, 1H), 1.44 (d, J=10.6 Hz, 1H), 1.22 (s, 3H), 0.64 (s, 3H).

B. 2-Ethyl-6,6-dimethyl-bicyclo[3.1.1]heptane-3-carbonitrile

2-Acetyl-6,6-dimethyl-bicyclo[3.1.1]heptane-3-carbonitrile (551 mg, 2.88 mmol) was dissolved in methanol (20 ml) under an atmosphere of dry N$_2$. The reaction was then cooled to 0° C. to which sodium borohydride (203 mg, 5.37 mmol) was added. After stirring at 0° C. for two hours, the reaction was concentrated under vacuum and partitioned between saturated NaHCO$_3$ and CH$_2$Cl$_2$. The CH$_2$Cl$_2$ layer was dried over Na$_2$SO$_4$, filtered and concentrated under vacuum to give 2-(1-hydroxy-ethyl)-6,6-dimethyl-bicyclo [3.1.1]heptane-3-carbonitrile as a mixture of diastereomers. The mixture was then dissolved in anhydrous DMF (10 ml) under an atmosphere of dry N$_2$. To this reaction was added 1,1'-thiocarbonyl-diimidazole (990 mg, 5.00 mmol). After stirring at ambient temperature for 16 hours, the reaction was then partitioned between 1.0% sodium bisulfate solution and ethyl ether. The ethyl ether layer was washed twice with water, once with brine, dried over MgSO$_4$, filtered and concentrated under vacuum to give imidazole-1-carbothioic acid-O-[1-(3-cyano-6,6-dimethyl-bicyclo(3.1.1]hept-2-yl)-ethyl] ester as a mixture of diastereomers. The mixture was then dissolved in anhydrous toluene (10 ml) under an atmosphere of dry N$_2$. To this mixture was added α,α'-azoisobutyronitrile (250 mg, 1.52 mmol) and tributyltin hydride (2.0 ml, 7.21 mmol). The reaction was then heated to 100° C. . After stirring at 100° C. for 3 hours, the reaction was concentrated under vacuum to give an oil. The oil was chromatographed on silica gel using hexanes to remove the bulk of the tin containing species and then eluting with 1% ethyl acetate in hexanes to give 288 mg of the titled compound: $^1$H NMR (CDCl$_3$)δ 2.72 (dt, J=6.8, 9.8 Hz, 1H), 2.37–2.47 (m, 2H), 2.13–22 (m, 2H) 2.00 (m, 2H), 1.60 (m, 1H), 1.21–1.38 (m, 2H), 1.20 (s, 3H), 0.98 (t, J=7.2 Hz, 3H), 0.91 (s, 3H).

C. C-(2-Ethyl-6,6-dimethyl-bicyclo[3.1.1]hept-3-yl)-methylamine

2-Ethyl-6,6-dimethyl-bicyclo[3.1.1]heptane-3-carbonitrile (288 mg, 1.65 mmol) was dissolved in anhydrous THF (10 ml) under an atmosphere of dry $N_2$. To the reaction was added a 1.0 M solution of lithium aluminum hydride (4.0 ml) in THF. The reaction was stirred at ambient temperature for 16 hr and was then quenched by the sequential slow addition of 152 μl of water, 152 μl of 15% NaOH and finally 460 μl of water. The reaction was stirred for an additional 2 hr after which time it was filtered and the filter cake was washed with $CH_2Cl_2$. The combined filtrate was concentrated under vacuum to give 267 mg of the titled compound: $^1$H NMR ($CD_3OD$) 6 2.73 (dd, J=4.6,12.2 Hz, 1H), 2.41 (dd, J=9.5, 12.2 Hz, 1H), 2.32 (m, 1H), 2.19 (m, 1H), 1.98 (m, 1H), 1.91 (m, 1H), 1.74 (m, 1H), 1.28–1.57 (m, 4H), 1.20 (s, 3H), 0.99 (s, 3H), 0.89 (t, J=7.2 Hz, 3H), 0.74 (d, J=9.6 Hz, 1H).

D. 4-{[1-(2-Ethyl-6,6-dimethyl-bicyclo[3.1.1]hept-3-ylmethyl)-5-Oxo-4,4-bis-pyridin-4-ylmethyl-imidazolidin-2-ylidene]-acetyl}-benzonitrile The same procedure that was used in example 1 was followed except that 2-ethyl-3-isothiocyanatomethyl-6,6-dimethyl-bicyclo[3.1.1]heptane was used in the place of (+)-3-pinanemethyl isothiocyanate in step D to give the titled compound as a tan solid. 2-Ethyl-3-isothiocyanatomethyl-6,6-dimethyl-bicyclo[3.1.1]heptane was prepared by using C-(2-ethyl-6,6-dimethyl-bicyclo[3.1.1]hept-3-yl)-methylamine in the place of 2-adamantan-1-yl-ethylamine in step A of example 15: C.I. m/z 574.3 [M+1]; $^1$H NMR ($CDCl_3$)δ 10.46 (br s, 1H), 8.45 (m, 4H), 7.81 (d, J=8.4 Hz, 2H), 7.70 (d, J=8.4 Hz, 2H), 7.12 (m, 4H), 5.23 (s, 1H), 3.25 (d, J=13.3 Hz, 2H), 3.04–3.20 (m, 3H), 2.88 (dd, J=4.0, 13.7 Hz, 1H), 2.27 (m, 1H), 1.92 (m, 1H), 1.72 (m, 2H), 1.16–1.41 (m, 4H), 1.11 (s, 3H), 0.95 (m, 1H), 0.87 (m, 3H), 0.77 (s, 3H), 0.60 (d, J=10.0 Hz, 1H).

EXAMPLE 43

4-[1-(2-Benzyl-6,6-dimethyl-bicyclo[3.1.1]hept-3-ylmethyl)-5-Oxo-4,4-bis-pyridin-4-ylmethyl-imidazolidin-2-ylidene]-acetyl}-benzonitrile The same procedure that was used in example 1 was followed except that 2-benzyl-3-isothiocyanatomethyl-6,6-dimethyl-bicyclo[3.1.1]heptane was used in the place of (+)-3-pinanemethyl isothiocyanate in step D to give the titled compound as a tan solid. 2-Benzyl-3-isothiocyanatomethyl-6,6-dimethyl-bicyclo[3.1.1]heptane was prepared by using (6,6-dimethyl-bicyclo[3.1.1]hept-2-en-2-yl)-phenyl-methanone in the place of 3-(3-ethyl-2,2-dimethyl-cyclobutyl)-but-3-en-2-one in example 42: C.I. m/z 636 [M+1]; $^1$H NMR ($CDCl_3$)δ 10.46 (br s, 1H), 8.46 (m, 4H), 7.82 (d, J=8.5 Hz, 2H), 7.71 (d, J=8.5 Hz, 2H), 7.06–7.24 (m, 9H), 5.15 (s, 1H), 3.23 (dd, J=3.1, 13.3 Hz, 2H), 3.03–3.11 (m, 3H), 2.72 (dd, J=4.8, 13.9 Hz, 1H), 2.60 (m, 2H), 2.20 (m, 1H), 1.91 (m, 1H), 1.66–1.76 (m, 5H), 1.11 (s, 3H), 0.94 (s, 3H), 0.55 (d, J=10.0 Hz, 1H).

EXAMPLE 44

4-{[1-(2-Isopropenyl-6,6-dimethyl-bicyclo[3.1.1]hept-3-ylmethyl)-5-Oxo-4,4-bis-pyridin-4-ylmethyl-imidazolidin-2-ylidene]-acetyl}-benzonitrile A. 2-Isopropenyl-6,6-dimethyl-bicyclo[3.1.1]heptane-3-carbonitrile Methyltriphenylphosphonium iodide (3.17 g, 7.84 mmol) was suspended in anhydrous THF (20 ml) under an atmosphere of dry $N_2$. To this solution was added a 1.0 M solution of potassium tert-butoxide (7.84 ml) in THF. After the reaction has stirred at ambient temperature for 30 min, a solution of 2-acetyl-6,6-dimethyl-bicyclo[3.1.1]heptane-3-carbonitrile (1.00 g, 5.23 mmol), prepared in step A of example 42, dissolved in anhydrous THF (10 ml) was added to the reaction. After stirring for two hours, the reaction was then partitioned between ethyl ether and water. The ethyl ether layer was washed with brine, dried over $MgSO_4$, filtered and concentrated under vacuum to give an oil which was chromatographed on silica gel using a gradient of neat hexanes to 10% ethyl acetate in hexanes to give 490 mg of the titled compound as an oil: C.I. m/z 190 [M+1]; $^1$H NMR ($CDCl_3$)δ 4.82 (m, 2H), 2.82 (m, 2H), 2.10–2.28 (m, 3H), 1.93 (m, 2H), 1.75 (s, 3H), 1.33 (d, J=9.9 Hz, 1H), 1.23 (s, 3H), 0.93 (s, 3H), 0.80–0.87 (m, 2H).

B. 4-{[1-(2-Isopropenyl-6,6-dimethyl-bicyclo[3.1.1]hept-3-ylmethyl)-5-Oxo-4,4-bis-pyridin-4-ylmethyl-imidazolidin-2-ylidene]-acetyl}-benzonitrile The same procedure that was used in example 1 was followed except that 2-isopropenyl-3-isothiocyanatomethyl-6,6-dimethyl-bicyclo[3.1.1]heptane was used in the place of (+)-3-pinanemethyl isothiocyanate in step D to give the titled compound as a tan solid. 2-Isopropenyl-3-isothiocyanatomethyl-6,6-dimethyl-bicyclo[3.1.1]heptane was prepared by reducing 2-isopropenyl-6,6-dimethyl-bicyclo[3.1.1]heptane-3-carbonitrile to the requisite amine following the procedure in step C of example 42 and subsequently converted to the isothiocyanate using step A of example 15: C.I. m/z 586 [M+1]; $^1$H NMR ($CDCl_3$)δ 10.47 (br s, 1H), 8.43–8.49 (m, 4H), 7.82 (d, J=8.7 Hz, 2H), 7.69 (d, J=8.7 Hz, 2H), 7.13 (m, 2H), 7.08 (m, 2H), 5.27 (s, 1H), 4.74 (m, 2H), 3.33 (dd, J=11.2, 13.9 Hz, 1H), 3.23 (d, J=13.5 Hz, 2H), 3.03–3.15 (m, 2H), 2.84 (dd, J=3.2, 13.9 Hz, 1H), 1.99–2.15 (m, 2H), 1.70 (m, 3H), 1.63 (s, 3H), 1.20 (m, 2H), 1.15 (s, 3H), 0.77(s, 3H), 0.66 (m, 1H).

EXAMPLE 45

4-{[1-(2-Isopropyl-6,6-dimethyl-bicyclo[3.1.1]hept-3-ylmethyl)-5-Oxo-4,4-bis-pyridin-4-ylmethyl-imidazolidin-2-ylidene]-acetyl}-benzonitrile A. 2-isopropyl-6,6-dimethyl-bicyclo[3.1.1]heptane-3-carbonitrile.

2-Isopropenyl-6,6-dimethyl-bicyclo[3.1.1]heptane-3-carbonitrile (233 mg, 1.23 mmol), prepared in step A of example 44, was dissolved in absolute ethanol (10 ml). To the solution was added 10% palladium on activated carbon (40 mg) and the reaction was subsequently shaken on a Paar apparatus under an atmosphere of 45 psi of hydrogen (H2). After shaking for 16 hours, the reaction was filtered through celite. The celite was washed with copious amounts of absolute ethanol. The combined filtrate was concentrated under vacuum to give the titled compound as an oil: $^1$H NMR ($CDCl_3$)δ 2.62 (q, J=9.3 Hz, 1H), 2.24 (m, 1H), 2.06–2.15 (m, 2H), 2.00 (m, 1H), 1.83–1.94 (m, 2H), 1.67 (quin, J=6.7 Hz, 1H), 1.21 (s, 3H), 1.15 (d, J=10.8 Hz, 1H), 0.98 (d, J=6.8 Hz, 3H), 0.87 (m, 6H).

B. 4-{[1-(2-Isopropyl-6,6-dimethyl-bicyclo[3.1.1]hept-3-ylmethyl)-5-Oxo-4,4-bis-pyridin-4-ylmethyl-imidazolidin-2-ylidene]-acetyl}-benzonitrile The same procedure that was used in example 1 was followed except that 2-isopropyl-3-isothiocyanatomethyl-6,6-dimethyl-bicyclo[3.1.1]heptane was used in the place of (+)-3-pinanemethyl isothiocyanate in step D to give the titled compound as a tan solid. 2-Isopropyl-3-isothiocyanatomethyl-6,6-dimethyl-bicyclo[3.1.1]heptane was prepared by reduction of 2-isopropyl-6,6-dimethyl-bicyclo[3.1.1]heptane-3-carbonitrile to the requisite amine following the procedure in step C of example 42 and subsequent conversion to the isothiocyanate using step A of example 15: C.I. m/z 588 [M+1]; $^1$H NMR (CDCl$_3$)δ 10.45 (br s, 1H), 8.42–8.46 (m, 4H), 7.82 (d, J=8.1 Hz, 2H), 7.69 (d, J=8.1 Hz, 2H), 7.13 (m, 2H), 7.07 (m, 2H), 5.22 (s, 1H), 3.32 (dd, J=11.2, 13.9 Hz, 1H), 3.24 (d, J=13.1 Hz, 2H), 3.01–3.10 (m, 2H), 2.92 (dd, J=3.1, 13.9 Hz, 1H), 1.96 (m, 1H), 1.76 (m, 1H), 1.59–1.70 (m, 3H), 1.32 (m, 1H), 1.24 (m, 1H), 1.14 (s, 3H), 1.05 (d, 10.2 Hz, 1H), 0.86 (d, J=6.6 Hz, 3H), 0.78 (d, J=6.9 Hz, 3H), 0.70 (s, 3H), 0.50 (m, 1H).

EXAMPLE 46

4-((1-[2-(1-Methoxyimino-ethyl)-6,6-dimethyl-bicyclo[3.1.1]hept-3-ylmethyl]-5-Oxo-4,4-bis-pyridin-4-ylmethyl-imidazolidin-2-ylidene}-acetyl)-benzonitrile A. (2-Acetyl-6,6-dimethyl-bicyclo[3.1.1]hept-3-ylmethyl)-carbamic acid tert-butyl ester 2-Acetyl-6,6-dimethyl-bicyclo[3.1.1]heptane-3-carbonitrile (400 mg, 2.09 mmol), prepared in step A of example 42, was dissolved in anhydrous THF (20 ml) under an atmosphere of dry N$_2$. The solution was cooled to –78° C. after which time a 1.0 M lithium aluminum hydride in THF (8.5 ml) was added to the reaction. The reaction was then warmed up to ambient temperature. After stirring at ambient temperature for 16 hours, the solution was cooled to 0° C. and the reaction was quenched with the successive slow addition of 310 μl of water, 310 μl of 15% NaOH and finally 1.0 ml of water. The solution was then stirred for two hours after which time it was filtered and the filter cake was washed with CH$_2$Cl$_2$. The combined filtrate was concentrated under vacuum and then dissolved in anhydrous CH$_2$Cl$_2$ (20 ml) under an atmosphere of dry N$_2$. To this solution was added di-tert-butyl dicarbonate (556 mg, 2.55 mmol). After stirring at ambient temperature for 16 hours, the reaction was then concentrated under vacuum and chromatographed on silica gel using 30% ethyl acetate in hexanes to give 420 mg of [2-(1-hydroxy-ethyl)-6,6-dimethyl-bicyclo[3.1.1]hept-3-ylmethyl]-carbamic acid tert-butyl ester as a mixture of diastereomers. A portion of the mixture (370 mg, 1.25 mmol) was dissolved in anhydrous CH$_2$Cl$_2$ (10 ml) under an atmosphere of dry N$_2$ to which was added 4-methylmorpholine N-oxide (262 mg, 2.24 mmol) and tetrapropylammonium perruthenate (39 mg, 0.12 mmol). The mixture was stirred at ambient temperature for 2.5 hours after which time it was passed through a silica gel plug eluting with CH$_2$Cl$_2$ then switching to ethyl acetate. The filtrate was concentrated under vacuum to give 370 mg of the titled compound as an oil: C.I. m/z 196 [M+1-Boc].

B. 1-(3-Aminomethyl-6,6-dimethyl-bicyclo[3.1.1]hept-2-yl)-ethanone-O-methyl-oxime (2-Acetyl-6,6-dimethyl-bicyclo[3.1.1]hept-3-ylmethyl)-carbamic acid tert-butyl ester (370 mg, 1.25 mmol) was dissolved in absolute ethanol (10 ml) under an atmosphere of dry N$_2$. To this solution was added methoxylamine hydrochloride (236 mg, 2.82 mmol) and pyridine (400 μl, 4.64 mmol). After stirring at ambient temperature for 20 hours, the mixture was concentrated under vacuum and then partitioned between CH$_2$Cl$_2$ and 1% NaHSO$_4$. The CH$_2$Cl$_2$ layer was then washed with saturated NaHCO3 and brine. The solution was then dried over MgSO$_4$, filtered and concentrated under vacuum to give 349 mg of an oil. The oil was treated with trifluoroacetic acid (5.0 ml) for 20 minutes. The reaction was then concentrated under vacuum and partitioned between 0.1N NaOH and CH$_2$Cl$_2$. The CH$_2$Cl$_2$ layer was dried over Na$_2$SO$_4$, filtered and concentrated under vacuum to give 221 mg of the titled compound as an oil: C.I. m/z 225 [M+1]; $^1$H NMR (CDCl$_3$)δ 3.82 (s, 3H), 2.95 (m, 1H), 2.67 (m, 2H), 2.37 (m, 2H), 2.24 (m, 2H), 1.84–2.00 (m, 2H), 1.81 (s, 3H), 1.50 (m, 1H), 1.25 (m, 1H), 1.19 (s, 3H), 0.93 (s, 3H), 0.89 (d, J=9.8 Hz, 1H).

C. 4-({1-[2-(1-Methoxyimino-ethyl)-6,6-dimethyl-bicyclo[3.1.1]hept-3-ylmethyl]-5-Oxo-4,4-bis-pyridin-4-ylmethyl-imidazolidin-2-ylidene)-acetyl)-benzonitrile The same procedure that was used in example 1 was followed except that 1-(3-isothiocyanatomethyl-6,6-dimethyl-bicyclo[3.1.1]hept-2-yl)-ethanone O-methyl-oxime was used in the place of (+)-3-pinanemethyl isothiocyanate in step D to give the titled compound as a tan solid. 1-(3-isothiocyanatomethyl-6,6-dimethyl-bicyclo[3.1.1]hept-2-yl)-ethanone O-methyl-oxime was prepared by using 1-(3-aminomethyl-6,6-dimethyl-bicyclo[3.1.1]hept-2-yl)-ethanone O-methyl-oxime in the place of 2-adamantan-1-yl-ethylamine in step A of example 15: C.I. m/z 617 [M+1]; $^1$H NMR (CDCl$_3$)δ 10.47 (br s, 1H), 8.48 (m, 4H), 7.89 (d, J=8.3 Hz, 2H), 7.70 (d, J=8.3 Hz, 2H), 7.12 (m, 4H), 5.51 (s, 1H),3.58 (s, 3H), 2.94–3.40 (m, 6H), 2.44 (m, 1H), 2.14-2.36 (m, 2H), 1.76 (m, 1H), 1.74 (s, 3H), 1.18–1.26 (m, 2H), 1.14 (s, 3H), 1.00 (m, 1H), 0.85 (m, 1H), 0.75 (s, 3H).

EXAMPLE 47

4-{[1-(6,6-Dimethyl-2-methylene-bicyclo[3.1.1]hept-3-ylmethyl)-5-oxo-4,4-bis-pyridin-4-ylmethyl-imidazolidin-2-ylidene]-acetyl}-benzonitrile A. (6,6-Dimethyl-2-methylene-bicyclo[3.1.1]hept-3-ylmethyl)-acetic acid (6,6-Dimethyl-2-methylene-bicyclo[3.1.1]hept-3-ylmethyl)-acetic acid ethyl ester (3.25 g, 14.6 mmol) was dissolved in absolute ethanol (50 ml). To this solution was added 1.0 N NaOH (20 ml). After stirring for 18 hours at ambient temperature, the reaction was then concentrated to 20 ml and partitioned between 0.1 N HCl and CH$_2$Cl$_2$. The CH$_2$Cl$_2$ layer was dried over MgSO$_4$, filtered and concentrated under vacuum to give 2.79 g of the titled compound: C.I. m/z 195.1 [M+1]; $^1$H NMR (CDCl$_3$)δ 4.78 (s, 1H), 4.77 (s, 1H), 3.02 (s, 1H), 2.75 (dd, J=4.9, 15.3 Hz, 1H), 2.56 (d, J=10.9 Hz, 1H), 2.49 (t, J=6.1 Hz, 1H), 2.38 (m, 1H), 2.24 (dt, 2.1, 12.0 Hz, 1H), 2.02 (m, 1H), 1.57 (dt, J=3.2,14.0 Hz, 1H), 1.26 (s, 3H), 1.19 (d, J=10.1,1H), 0.77 (s, 3H).

B. (6,6-Dimethyl-2-methylene-bicyclo[3.1.1]hept-3-ylmethyl)-carbamic acid benzyl ester (6,6-Dimethyl-2-methylene-bicyclo[3.1.1]hept-3-ylmethyl)-acetic acid (7.00 g, 36.1 mmol) was dissolved in anhydrous toluene (200 ml) under an atmosphere of dry N$_2$. To this solution was added triethylamine (6.10 ml, 43.6 mmol) and diphenylphosphoryl azide (9.30 ml, 42.1 mmol). The reaction was stirred for two hours at ambient temperature after which time benzyl alcohol (4.50 ml, 43.5 mmol) was added. The reaction was subsequently heated to 100° C. and stirred at this temperature for 3.5 hours. The reaction temperature was then cooled to 70° C. and stirred at this temperature for 18 hours. The reaction was then partitioned between 0.1 N NaOH and ethyl ether. The ethyl ether layer was washed with brine, dried over MgSO$_4$, filtered and concentrated under vacuum to give a brown oil. The oil was chromatographed on silica gel using a gradient starting from 8% ethyl acetate in hexanes to 12% ethyl acetate in hexanes to give 7.81 g of the titled compound as an oil: C.I. m/z 300.3 [M+1]; $^1$ H NMR (CDCl$_3$)δ 7.28–7.35 (m, 5H), 5.09 (s, 2H), 4.72 (s, 2H), 3.29 (m, 2H), 2.66 (m, 1H), 2.43 (m, 1H), 2.32 (m, 1H), 1.98–2.06 (m, 2H), 1.57 (m, 1H), 1.23 (s, 3H), 1.17 (d, J=10.1, 1H), 0.72 (s, 3H).

C. C-(6,6-Dimethyl-2-methylene-bicyclo[3.1.1]hept-3-ylmethyl)-methylamine (6,6-Dimethyl-2-methylene-bicyclo[3.1.1]hept-3-ylmethyl)-carbamic acid benzyl ester (988 mg, 3.30 mmol) was dissolved in $CH_2Cl_2$ (20 ml) under an atmosphere of dry $N_2$. To this solution was added triethylsilane (2.10 ml, 13.2 mmol), triethylamine (330 μl, 2.37 mmol) and palladium(II) chloride (165 mg). The reaction was then heated to reflux and stirred at this temperature for one hour. The reaction was then quenched with the addition of saturated ammonium chloride solution (3.0 ml). The reaction is then partitioned between $CH_2Cl_2$ and 0.1 N NaOH. The $CH_2Cl_2$ layer was dried over $MgSO_4$, filtered and concentrated under vacuum to give the titled compound along with unreacted triethylsilane: C.I. m/z 166 [M+1].

D. 4-{[1-(6,6-Dimethyl-2-methylene-bicyclo[3.1.1]hept-3-ylmethyl)-5-oxo-4,4-bis-pyridin-4-ylmethyl-imidazolidin-2-ylidene]-acetyl}-benzonitrile The same procedure that was used in example 1 was followed except that 3-isothiocyanatomethyl-6,6-dimethyl-2-methylene-bicyclo[3.1.1]heptane was used in the place of (+)-3-pinanemethyl isothiocyanate in step D to give the titled compound as a tan solid. 3-Isothiocyanatomethyl-6,6-dimethyl-2-methylene-bicyclo[3.1.1]heptane was prepared by using C-(6,6-dimethyl-2-methylene-bicyclo[3.1.1]hept-3-ylmethyl)-methylamine in the place of 2-adamantan-1-yl-ethylamine in step A of example 15: C.I. m/z 558 [M+1]; $^1$H NMR ($CDCl_3$)δ 10.46 (br s, 1H), 8.49 (m, 4H), 7.84 (d, J=8.4 Hz, 2H), 7.70 (d, J=8.4 Hz, 2H), 7.11 (m, 4H), 5.27 (s, 1H), 4.68 (s, 1H), 4.50 (s, 1H), 3.00–3.38 (m, 6H), 2.28–2.57 (m, 3H), 1.86 (m, 1H), 0.80–1.30 (m, 6H), 0.60 (s, 3H).

EXAMPLE 48

4-{[1-(2-Hydroxy-2-hydroxymethyl-6,6-dimethyl-bicyclo[3.1.1]hept-3-ylmethyl)-5-oxo-4,4-bis-pyridin-4-ylmethyl-imidazolidin-2-ylidene]-acetyl}-benzonitrile A. (2-Hydroxy-2-hydroxymethyl-6,6-dimethyl-bicyclo[3.1.1]hept-3-ylmethyl)-carbamic acid benzyl ester (6,6-Dimethyl-2-methylene-bicyclo[3.1.1]hept-3-ylmethyl)-carbamic acid benzyl ester (2.19 g, 7.32 mmol), prepared in step B of example 47, was dissolved in $CH_2Cl_2$ (50 ml). To this solution was added trimethylamine N-oxide dihydrate (894 mg, 8.79 mmol) and osmium tetroxide (136 mg, 0.535 mmol). The solution was stirred at ambient temperature for 16 hours after which time the reaction was concentrated under vacuum and chromatographed on silica gel using a gradient starting with 30% ethyl acetate in hexanes to 50% ethyl acetate in hexanes to give 1.51 g of the titled compound as a brown oil: C.I. m/z 316 [M+1-$H_2O$]; $^1$H NMR ($CDCl_3$)δ 7.31–7.39 (m, 5H), 5.59 (br s, 1H), 5.12 (s, 2H), 3.30–3.58 (m, 4H), 1.93–2.28 (m, 4H), 1.52 (m, 1H), 1.24–1.30 (m, 5H), 0.96 (s, 3H).

B. The acetonide of (2-hydroxy-2-hydroxymethyl-6,6-dimethyl-bicyclo[3.1.1]hept-3-ylmethyl)-carbamic acid benzyl ester (2-Hydroxy-2-hydroxymethyl-6,6-dimethyl-bicyclo[3.1.1]hept-3-ylmethyl)-carbamic acid benzyl ester (1.46 g, 4.38 mmol) was dissolved in $CH_2Cl_2$ (20 ml) under an atmosphere of dry $N_2$. To the solution was added 2,2-dimethoxypropane (20 ml) and acetyl chloride (50 μl). The mixture was stirred for 16 hours at ambient temperature after which time it was partitioned between $CH_2Cl_2$ and saturated $NaHCO_3$. The $CH_2Cl_2$ layer was washed with brine, dried over $MgSO_4$, filtered and concentrated under vacuum to give 1.44 g of the titled compound as a brown oil: C.I. m/z 374 [M+1]; $^1$H NMR ($CDCl_3$)δ 7.31–7.39 (m, 5H), 5.51 (br s, 1H), 5.07 (m, 2H), 3.91 (d, J=8.5 Hz, 1H), 3.63 (d, J=8.5 Hz, 1H), 3.53 (m, 1H), 3.19 (dt, J=4.7, 13.8 Hz, 1H), 2.23 (m, 2H), 2.08 (m, 1H), 1.93 (m, 2H), 1.71 (m, 1H), 1.36 (s, 6H), 1.24 (s, 3H), 0.91 (s, 3H).

C. The acetonide of C-(2-hydroxy-2-hydroxymethyl-6,6-dimethyl-bicyclo[3.1.1]hept-3-ylmethyl)-methylamine (8-Ethyl-2,2,9,9-tetramethyl-1,3-dioxa-spiro[4.5]dec-6-ylmethyl)-carbamic acid benzyl ester (1.41 g, 3.78 mmol) was dissolved in absolute ethanol (35 ml). To the solution was added acetic acid (430 μl) and 20% palladium hydroxide on carbon (150 mg). The reaction was then shaken on a Paar apparatus under an atmosphere of 50 psi of $H_2$. After shaking for 45 min, the reaction was filtered through celite and the celite was washed with copious amounts of absolute ethanol. The pH of the filtrate was adjusted to 8 with saturated $NaHCO_3$ and then concentrated under vacuum. The resulting residue was partitioned between $CH_2Cl_2$ and 0.1 N NaOH. The $CH_2Cl_2$ layer was dried over $Na_2SO_4$, filtered and concentrated under vacuum to give 720 mg of the titled compound as a brown oil: C.I. m/z 240 [M+1]; $^1$H NMR ($CDCl_3$)δ 3.91 (d, J=8.5 Hz, 1H), 3.68 (d, J=8.5 Hz, 1H), 2.82 (m, 2) 1.98–2.25 (m, 5H), 1.72 (m, 1H), 1.38 (s, 3H), 1.36 (s, 3H), 1.29 (d, J=10.0 Hz, 1H), 1.24 (s, 3H), 0.93 (s, 3H).

D. 4-{[1-(2-Hydroxy-2-hydroxymethyl-6,6-dimethyl-bicyclo[3.1.1]hept-3-ylmethyl)-5-oxo-4,4-bis-pyridin-4-ylmethyl-imidazolidin-2-ylidene]-acetyl}-benzonitrile The same procedure that was used in example 1 was followed except that the acetonide of 3-isothiocyanatomethyl-2-hydroxy-2-hydroxymethyl-6,6-dimethyl-2-methylene-bicyclo[3.1.1]heptane was used in the place of (+)-3-pinanemethyl isothiocyanate in step D to give a tan solid which was then dissolved in 0.1 N HCl. After stirring for 16 hours at ambient temperature, the reaction was processed in the same manner as in step F in example 1 to give the titled compound as a tan solid. The acetonide of 3-isothiocyanatomethyl-2-hydroxy-2-hydroxymethyl-6,6-dimethyl-2-methylene-bicyclo[3.1.1]heptane was prepared by using the acetonide of C-(2-hydroxy-2-hydroxymethyl-6,6-dimethyl-bicyclo[3.1.1]hept-3-ylmethyl)-methylamine in the place of 2-adamantan-1-yl-ethylamine in step A of example 15: C.I. m/z 592 [M+1]; $^1$H NMR ($CDCl_3$)δ 8.47 (m, 4H), 7.98 (d, J=8.4 Hz, 2H), 7.72 (d, J=8.4 Hz, 2H), 7.16 (d, J=6.0 Hz, 2H), 7.11 (d, J=6.0 Hz, 2H), 5.71 (s, 1H), 3.03–3.49 (m, 8H), 2.41 (m, 1H), 2.18 (m, 1H), 2.05 (m, 1H), 1.83 (m, 2H), 1.26 (d, J=10.5 Hz, 1H), 1.18 (s, 3H), 1.08 (m, 1H), 0.74 (s, 3H).

EXAMPLE 49

4-{[1-(6,6-Dimethyl-2-oxo-bicyclo[3.1.1] hept-3-ylmethyl)-5-oxo-4,4-bis-pyridin-4-ylmethyl-imidazolidin-2-ylidene]-acetyl}-benzonitrile 4-{[1-(2-Hydroxy-2-hydroxymethyl-6,6-dimethyl-bicyclo[3.1.1]hept-3-ylmethyl)-5-oxo-4,4-bis-pyridin-4-ylmethyl-imidazolidin-2-ylidene]-acetyl}-benzonitrile (540 mg, 0.914 mmol), as prepared in example 48, was dissolved in 0.1 N HCl (5 ml). To this solution was added sodium periodate (235 mg, 1.10 mmol). After stirring at ambient temperature for 16 hours, the pH of the reaction was adjusted to 8 using $NaHCO_3$. The reaction was then partitioned between $CH_2Cl_2$ and saturated $NaHCO_3$. The $CH_2Cl_2$ was dried over $Na_2SO_4$, filtered and concentrated under vacuum to give a golden foam which was then chromatographed on silica gel using 60% acetone in hexanes to give 331 mg of the titled compound as a brown foam: C.I. m/z 560 [M+1]; $^1$H NMR (CDCl$_3$)δ 10.36 (br s, 1H), 8.48 (m, 4H), 7.94 (d, J=8.3 Hz, 2H), 7.74 (d, J=8.4 Hz, 2H), 7.14 (m, 4H), 5.49 (s, 1H), 3.46 (m, 2H), 3.29 (m, 2H), 3.09 (m, 2H), 2.52 (m, 2H), 2.24 (m, 1H), 2.18 (m, 1H), 1.49 (m, 1H), 1.29 (s, 3H), 1.19 (d, J=8.9 Hz, 1H), 0.89 (m, 1H), 0.76 (s, 3H).

What is claimed is:

1. A compound of the formula

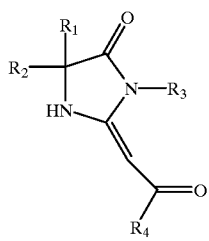

or a pharmaceutically acceptable salt thereof, wherein:

R$_1$ and R$_2$ are independently selected from the group consisting of —(CH$_2$)$_p$(5–10 membered heterocyclyl), —(CH$_2$)$_p$(C$_6$–C$_{10}$ aryl), allyl, propargyl and C$_1$–C$_6$ alkyl wherein p is 0 to 3, said alkyl and the alkyl moieties of said R$_1$ and R$_2$ groups are optionally substituted by 1 to 3 R$_9$ substituents, and the aryl and heterocyclyl moieties of said R$_1$ and R$_2$ groups are optionally substituted by 1 to 3 substituents independently selected from halo and R$_9$;

R$_3$ is —(CH$_2$)m(1- or 2-adamantyl), —(CH$_2$)$_m$(C$_3$–C$_{10}$ cycloalkyl), —(CH$_2$)m(C$_6$–C$_{10}$ aryl), C$_1$–C$_{10}$ alkyl,

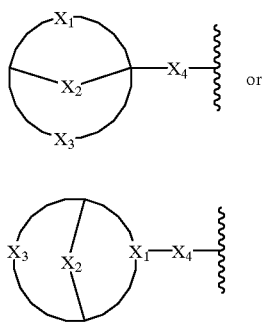

wherein m is 0 to 6, said cycloalkyl and alkyl optionally contain 1 or 2 double or triple bonds;

X$_1$, X$_2$, and X$_3$ are each independently C$_1$–C$_7$ alkylene optionally containing 1 or 2 double or triple bonds, X$_4$ is a bond or C$_1$–C$_7$ alkylene optionally containing 1 or 2 double or triple bonds, and, in formula (Ib), the X$_4$ moiety is attached to the X$_1$ moiety at any available carbon in the X$_1$ moiety;

R$_4$ is C$_6$–C$_{10}$ aryl, 5–10 membered heterocyclyl or C$_1$–C$_6$ alkyl wherein each of said R$_4$ groups is optionally substituted by 1 to 3 R$_5$ substituents;

each R$_5$ is independently selected from the group consisting of halo, nitro, cyano, phenyl, —C(O)OR$_6$, —SO$_2$NR$_6$R$_7$, —NR$_6$R$_8$, —C(O)R$_6$, —OR$_6$, —C(O)NR$_6$R$_8$, —OC(O)NR$_6$R$_8$, —NR$_8$C(O)NR$_8$R$_6$, —NR$_8$C(O)R$_6$, —NR$_8$C(O)O(C$_1$–C$_4$ alkyl), —C(NR$_8$)NR$_8$R$_6$, —C(NCN)NR$_8$R$_6$, —C(NCN)S(C$_1$–C$_4$ alkyl), —NR$_8$C(NCN)S(C(O)-C$_4$ alkyl), —NR$_8$C(NCN) NR$_8$R$_6$, —NR$_8$SO$_2$(C$_1$–C$_4$ alkyl), —S(O)$_n$(C$_1$–C$_4$ alkyl) wherein n is 0 to 2, —NR$_8$C(O)C(O)NR$_8$R$_6$, —NR$_8$C(O)C(O)R8, thiazolyl, imidazolyl, oxazolyl, pyrazolyl, triazolyl, tetrazolyl, and C$_1$–C$_4$ alkyl optionally substituted by 1 to 3 fluoro substituents;

each R$_6$ and R$_7$ is independently hydrogen or C$_1$–C$_4$ alkyl;

each R$_8$ is independently R$_6$ or —OR$_6$; and, each R$_9$ is independently selected from cyano, R$_6$, —OR$_6$, —OC(O)R$_6$, —C(O)OR$_6$, —C(O)NR$_6$R$_7$, —NR$_6$R$_7$, —NR$_6$R$_8$, —SO$_2$NR$_6$R$_7$, and C$_1$–C$_4$ alkyl substituted by hydroxy.

2. The compound of claim 1 wherein R$_1$ and R$_2$ are both —(CH$_2$)$_p$(5–10 membered heterocyclyl) wherein p is 1 or 2.

3. The compound of claim 2 wherein R$_1$ and R$_2$ are independently 2-, 3- or 4-pyridinylmethyl.

4. The compound of claim 3 wherein R$_1$ and R$_2$ are both 4-pyridinylmethyl.

5. The compound of claim 1 wherein R$_3$ is an aliphatic bicyclo moiety of the formula

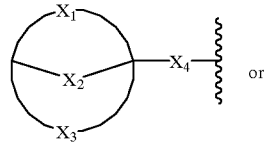

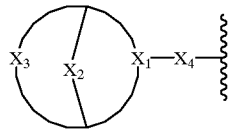

6. The compound of claim 5 wherein R$_3$ is —(CH$_2$)$_m$ (pinane) wherein m is 0, 1 or 2.

7. The compound of claim 6 wherein R$_3$ is pinanemethyl.

8. The compound of claim 4 wherein R$_4$ is phenyl optionally substituted by 1 to 3 R$_5$ substituents.

9. The compound of claim 1 wherein R$_1$ and R$_2$ are both 4-pyridinylmethyl and R$_3$ is —(CH$_2$)$_m$(pinane), wherein m is 0 to 2.

10. The compound of claim 9 selected from the group consisting of:

2-[2-(4-Bromo-phenyl)-2-oxo-ethylidene]-5,5-bis-pyridin-4-ylmethyl-3-(2,6,6-trimethyl-bicyclo[3.1.1] hept-3-ylmethyl)-imidazolidin-4-one;

4-{[5-Oxo-4,4-bis-pyridin-4-ylmethyl-1-(2,6,6-trimethyl-bicyclo[3.1.1]hept-3-ylmethyl)-imidazolidin-2-ylidene]-acetyl}-benzonitrile;

2-[2-(4-Chloro-phenyl)-2-oxo-ethylidene]-5,5-bis-pyridin-4-ylmethyl-3-(2,6,6-trimethyl-bicyclo[3.1.1] hept-3-ylmethyl)-imidazolidin-4-one;

2-[2-(3,4-Dichloro-phenyl)-2-oxo-ethylidene]-5,5-bis-pyridin-4-ylmethyl-3-(2,6,6-trimethyl-bicyclo[3.1.1] hept-3-ylmethyl)-imidazolidin-4-one;

2-[2-(3-Nitro-phenyl)-2-oxo-ethylidene]-5,5-bis-pyridin-4-yl methyl-3-(2,6,6-trimethyl-bicyclo[3.1.1]hept-3-ylmethyl)-imidazolidin-4-one;

2-[2-(4-Methoxy-phenyl)-2-oxo-ethylidene]-5,5-bis-pyridin-4-ylmethyl-3-(2,6,6-tri methyl-bicyclo[3.1.1] hept-3-ylmethyl)-imidazolidin-4-one;

2-[2-(3-Methoxy-phenyl)-2-oxo-ethylidene]-5,5-bis-pyridin-4-ylmethyl-3-(2,6,6-trimethyl-bicyclo[3.1.1] hept-3-ylmethyl)-imidazolidin-4-one;

2-[2-(2-Methoxy-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one;

2-(2-Biphenyl-4-yl-2-oxo-ethylidene)-5,5-bis-pyridin-4-ylmethyl-3-(2,6,6-trimethyl-bicyclo[3.1.1]hept-3-ylmethyl)-imidazolidin-4-one;

2-(2-Naphthalen-2-yl-2-oxo-ethylidene)-5,5-bis-pyridin-4-ylmethyl-3-(2,6,6-trimethyl-bicyclo[3.1.1]hept-3-ylmethyl)-imidazolidin-4-one;

2-[2-(4-Fluoro-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one;

2-[2-(2,4-Difluoro-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one;

4-{[5-Oxo-4,4-bis-pyridin-4-ylmethyl-1-(2,6,6-trimethyl-bicyclo[3.1.1]hept-3-yl)-imidazolidin-2-ylidene]-acetyl}-benzonitrile;

2-[2-(4-Nitro-phenyl)-2-oxo-ethylidene]-5,5-bis-pyridin-4-ylmethyl-3-(2,6,6-tri methyl-bicyclo[3.1.1]hept-3-ylmethyl)-imidazolidin-4-one;

2-[2-Oxo-2-phenyl-ethylidene]-5,5-bis-pyridin-4-ylmethyl-3-(2,6,6-trimethyl-bicyclo[3.1.1]hept-3-ylmethyl)-imidazolidin-4-one;

2-{2-Oxo-2-[4-(2H-tetrazol-5-yl)-phenyl]-ethylidene}-5,5-bis-pyridin-4-ylmethyl-3-(2,6,6-trimethyl-bicyclo[3.1.1]hept-3-ylmethyl)-imidazolidin-4-one;

3-{[5-Oxo-4,4-bis-pyridin-4-ylmethyl-1-(2,6,6-trimethyl-bicyclo[3.1.1]hept-3-ylmethyl)-imidazolidin-2-ylidene]-acetyl}-benzonitrile;

4-{[5-Oxo-4,4-bis-pyridin-4-ylmethyl-1-(2,6,6-trimethyl-bicyclo[3.1.1]hept-3-ylmethyl)-imidazolidin-2-ylidene]-acetyl}-benzoic acid ethyl ester;

2-[2-Oxo-2-(4-trifluoromethyl-phenyl)-ethylidene]-5,5-bis-pyridin-4-ylmethyl-3-(2,6,6-trimethyl-bicyclo[3.1.1]hept-3-ylmethyl)-imidazolidin-4-one;

2-[2-(4-Methanesulphonyl-phenyl)-2-oxo-ethylidene]-5,5-bis-pyridin-4-ylmethyl-3-(2,6,6-trimethyl-bicyclo[3.1.1]hept-3-ylmethyl)-imidazolidin-4-one; and, pharmaceutically acceptable salts of the foregoing compounds.

11. The compound of claim 5 wherein $R_1$ and $R_2$ are both 4-pyridinylmethyl.

12. The compound of claim 11 selected from the group consisting of:

4-{[1-(6,6-Dimethyl-bicyclo[3.1.1]hept-2-ylmethyl)-5-oxo-4,4-bis-pyridin-4-ylmethyl-imidazolidin-2-ylidene]-acetyl}-benzonitrile;

4-[(1-Bicyclo[2.2.2]oct-1-yl methyl-5-oxo-4,4-bis-pyridin-4-ylmethyl-imidazolidin-2-ylidene)-acetyl]-benzonitrile;

4-{[1-(2-Ethyl-6,6-dimethyl-bicyclo[3.1.1]hept-3-ylmethyl)-5-oxo-4,4-bis-pyridin-4-ylmethyl-imidazolidin-2-ylidene]-acetyl}-benzonitrile;

4-{[1-(2-Benzyl-6,6-dimethyl-bicyclo[3.1.1]hept-3-ylmethyl)-5-oxo-4,4-bis-pyridin-4-ylmethyl-imidazolidin-2-ylidene]-acetyl}-benzonitrile;

4-([1-(2-Isopropenyl-6,6-dimethyl-bicyclo[3.1.1]hept-3-ylmethyl)-5-oxo-4,4-bis-pyridin-4-ylmethyl-imidazolidin-2-ylidene]-acetyl}-benzonitrile;

4-{[1-(2-isopropyl-6,6-dimethyl-bicyclo[3.1.1]hept-3-ylmethyl)-5-oxo-4,4-bis-pyridin-4-ylmethyl-imidazolidin-2-ylidene]-acetyl}-benzonitrile;

4-({1-[2-(1-Methoxyimino-ethyl)-6,6-dimethyl-bicyclo[3.1.1]hept-3-ylmethyl]-5-oxo-4,4-bis-pyridin-4-ylmethyl-imidazolidin-2-ylidene}-acetyl)-benzonitrile;

4-{[1-(6,6-Dimethyl-2-methylene-bicyclo[3.1.1]hept-3-yl methyl)-5-oxo-4,4-bis-pyridin-4-ylmethyl-imidazolidin-2-ylidene]-acetyl}-benzonitrile;

4-{[1-(2-Hydroxy-2-hydroxymethyl-6,6-dimethyl-bicyclo[3.1.1]hept-3-ylmethyl)-5-oxo-4,4-bis-pyridin-4-ylmethyl-imidazolidin-2-ylidene]-acetyl}-benzonitrile;

4-{[1-(6,6-Dimethyl-2-oxo-bicyclo[3.1.1]hept-3-ylmethyl)-5-oxo-4,4-bis-pyridin-4-ylmethyl-imidazolidin-2-ylidene]-acetyl}-benzonitrile; and, pharmaceutically acceptable salts of the foregoing compounds.

13. The compound of claim 1 selected from the group consisting of:

3-tert-Butyl-2-(2-oxo-2-phenyl-ethylidene)-5,5-bis-pyridin-4-ylmethyl-imidazolidin-4-one;

4-{[1-(2,2-Dimethyl-propyl)-5-oxo-4,4-bis-pyridin-4-ylmethyl-imidazolidin-2-ylidene]-acetyl}-benzonitrile;

4-{[1-(2-Adamantan-1-yl-ethyl)-5-oxo-4,4-bis-pyridin-4-ylmethyl-imidazolidin-2-ylidene]-acetyl}-benzonitrile;

3-Cyclohexyl-2-(2-oxo-2-phenyl-ethylidene)-5,5-bis-pyridin-4-ylmethyl-imidazolidin-4-one;

4-[(1-Adamant-1-ylmethyl-5-Oxo-4,4-bis-pyridin-4-ylmethyl-imidazolidin-2-ylidene)-acetyl]-benzonitrile;

4-[(1-Cyclohexylmethyl-5-Oxo-4,4-bis-pyridin-4-ylmethyl-imidazolidin-2-ylidene]-acetyl-benzonitrile;

3-Hexyl-2-(2-oxo-2-phenyl-ethylidene)-5,5-bis-pyridin-4-ylmethyl-imidazolidin-4-one;

3-Napthalen-1-yl-2-(2-oxo-2-phenyl-ethylidene)-5,5-bis-pyridin-4-ylmethyl-imidazolidin-4-one;

3-Adamantan-1-yl-2-(2-oxo-2-phenyl-ethylidene)-5,5-bis-pyridin-4-ylmethyl-imidazolidin-4-one;

3-Adamantan-1-yl-2-[2-(4-nitro-phenyl)-2-oxo-ethylidene]-5,5-bis-pyridin-4-ylmethyl-imidazolidin-4-one;

4-[(1-Benzyl-5-oxo-4,4-bis-pyridin-4-ylmethyl-imidazolidin-2-ylidene)-acetyl]-benzonitrile;

4-[(1-Allyl-5-oxo-4,4-bis-pyridin-4-ylmethyl-imidazolidin-2-ylidene)-acetyl]-benzonitrile;

4-[(1-Methyl-5-oxo-4,4-bis-pyridin-4-ylmethyl-imidazolidin-2-ylidene)-acetyl]-benzonitrile;

4-{[1-(2,2-Diethoxy-ethyl)-5-Oxo-4,4-bis-pyridin-4-ylmethyl-imidazolidin-2-ylidene]-acetyl}-benzonitrile;

4-[(1-Adamantan-2-yl methyl-5-oxo-4,4-bis-pyridin-4-ylmethyl-imidazolidin-2-ylidene)-acetyl]-benzonitrile;

4-[(1-Adamantan-2-yl-5-oxo-4,4-bis-pyridin-4-ylmethyl-imidazolidin-2-ylidene)-acetyl]-benzonitrile;

4-[(5-Oxo-1-phenyl-4,4-bis-pyridin-4-ylmethyl-imidazolid in-2-ylidene)-acetyl]-benzonitrile;

4-{[4-tert-Butyl-phenyl-5-oxo-4,4-bis-pyridin-4-ylmethyl-imidazolidin-2-ylidene)-acetyl]-benzonitrile; and, pharmaceutically acceptable salts of the foregoing compounds.

14. A method of inhibiting abnormal cell growth in a mammal, comprising administering to said mammal an amount of a compound according to claim 1 that is effective in inhibiting farnesyl protein transferase.

15. The method of claim 14 wherein said abnormal cell growth is cancer.

16. The method of claim 15 wherein said cancer comprises lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma or pituitary adenoma.

17. The method of claim 14 wherein said abnormal cell growth is a benign proliferative disease.

18. The method of claim 17 wherein said benign proliferative disease comprises psoriasis, benign prostatic hypertrophy, or restinosis.

19. A pharmaceutical composition for inhibiting abnormal cell growth in a mammal, comprising an amount of a compound according to claim 1 that is effective in inhibiting farnesyl protein transferase and a pharmaceutically acceptable carrier.

20. A method of inhibiting abnormal cell growth in a mammal, comprising administering to said mammal an amount of a compound according to claim 1 that is effective in inhibiting abnormal cell growth.

21. The method of claim 20 wherein said abnormal cell growth is cancer.

22. The method of claim 21 wherein said cancer comprises lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma or pituitary adenoma.

23. The method of claim 20 wherein said abnormal cell growth is a benign proliferative disease.

24. The method of claim 23 wherein said benign proliferative disease comprises psoriasis, benign prostatic hypertrophy, or restinosis.

25. A pharmaceutical composition for inhibiting abnormal cell growth in a mammal, comprising an amount of a compound according to claim 1 that is effective in inhibiting abnormal cell growth and a pharmaceutically acceptable carrier.

26. The pharmaceutical composition of claim 25 wherein said abnormal cell growth is cancer.

* * * * *